(12) United States Patent
Widomski et al.

(10) Patent No.: US 8,361,111 B2
(45) Date of Patent: Jan. 29, 2013

(54) DEVICES, SYSTEMS AND METHODS FOR CLOSURE OF CARDIAC OPENINGS

(75) Inventors: David R. Widomski, Wakefield, MA (US); Carol A. Devellian, Topsfield, MA (US); Eileen M. Heneberry, Boston, MA (US); Andrzej J. Chanduszko, Chandler, AZ (US); Robert M. Carr, Paradise Valley, AZ (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 754 days.

(21) Appl. No.: 11/132,498

(22) Filed: May 19, 2005

(65) Prior Publication Data

US 2005/0216054 A1    Sep. 29, 2005

Related U.S. Application Data

(62) Division of application No. 11/045,026, filed on Jan. 27, 2005, now abandoned.

(60) Provisional application No. 60/540,474, filed on Jan. 30, 2004, provisional application No. 60/540,821, filed on Jan. 30, 2004, provisional application No. 60/540,827, filed on Jan. 30, 2004.

(51) Int. Cl.
*A61B 17/08* (2006.01)
(52) U.S. Cl. .................. 606/213; 606/194; 623/23.72
(58) Field of Classification Search ............... 623/23.73, 623/23.72; 606/213–216, 191, 194
See application file for complete search history.

(56) References Cited

U.S. PATENT DOCUMENTS 3,050,066 A    8/1962 Koehn
3,502,069 A    3/1970 Silverman
(Continued)

FOREIGN PATENT DOCUMENTS

EP    1013227    12/1999
EP    1 046 375 A1    10/2000
(Continued)

OTHER PUBLICATIONS

International Search Report for International Application No. PCT/US2005/003126, mailed Sep. 30, 2005, (7 pages).

(Continued)

*Primary Examiner* — Corrine M McDermott
*Assistant Examiner* — Gregory Anderson
(74) *Attorney, Agent, or Firm* — DLA Piper LLP (US)

(57) ABSTRACT

The invention generally relates to devices, systems, and methods for percutaneous closure of cardiac openings and obliteration of the cardiac cul-de-sacs. In one embodiment, a closure device includes a patch with an adhesive and/or a removable frame. The patch may be placed across a cardiac opening, such as a patent foramen ovale, or across a cardiac cul-de-sac, such as a left atrial appendage. In another embodiment, a closure device includes a balloon together with adhesives and/or substances for stimulating tissue growth coated on, or contained within, the balloon. The balloon may be inserted into a cardiac opening, such as the patent foramen ovale, or into a cardiac cul-de-sac, such as a left atrial appendage.

9 Claims, 26 Drawing Sheets

U.S. PATENT DOCUMENTS

| | | |
|---|---|---|
| 3,800,781 A | 4/1974 | Zalucki |
| 3,874,388 A | 4/1975 | King et al. |
| 3,875,648 A | 4/1975 | Bone |
| 3,924,631 A | 12/1975 | Mancusi |
| 4,006,747 A | 2/1977 | Kronenthal et al. |
| 4,007,743 A | 2/1977 | Blake |
| 4,271,839 A * | 6/1981 | Fogarty et al. ............... 606/194 |
| 4,425,908 A | 1/1984 | Simon |
| 4,479,497 A * | 10/1984 | Fogarty et al. ............... 606/194 |
| 4,606,347 A | 8/1986 | Fogarty et al. |
| 4,650,466 A | 3/1987 | Luther |
| 4,696,300 A | 9/1987 | Anderson |
| 4,710,192 A | 12/1987 | Liotta et al. |
| 4,836,204 A | 6/1989 | Landymore et al. |
| 4,900,303 A * | 2/1990 | Lemelson .................... 604/514 |
| 4,902,508 A | 2/1990 | Badylak et al. ............... 424/95 |
| 4,915,107 A | 4/1990 | Rebuffat et al. |
| 4,921,484 A | 5/1990 | Hillstead |
| 4,946,440 A | 8/1990 | Hall |
| 4,956,178 A | 9/1990 | Badylak et al. |
| 5,021,059 A | 6/1991 | Kensey et al. |
| 5,037,433 A | 8/1991 | Wilk et al. |
| 5,041,090 A * | 8/1991 | Scheglov et al. ........ 604/101.02 |
| 5,041,129 A | 8/1991 | Hayhurst et al. |
| 5,042,976 A | 8/1991 | Ishitsu et al. |
| 5,100,429 A | 3/1992 | Sinofsky et al. |
| 5,108,420 A | 4/1992 | Marks |
| 5,171,259 A | 12/1992 | Inoue |
| 5,176,687 A | 1/1993 | Hasson et al. |
| 5,192,301 A | 3/1993 | Kamiya et al. |
| 5,222,974 A | 6/1993 | Kensey et al. |
| 5,236,440 A | 8/1993 | Hlavacek |
| 5,257,637 A | 11/1993 | El Gazayerli |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,417 A | 5/1994 | Wilk |
| 5,312,435 A | 5/1994 | Nash et al. |
| 5,330,446 A * | 7/1994 | Weldon et al. ............... 604/271 |
| 5,334,217 A | 8/1994 | Das |
| 5,354,308 A | 10/1994 | Simon et al. |
| 5,370,647 A | 12/1994 | Graber et al. |
| 5,383,899 A * | 1/1995 | Hammerslag ............... 606/214 |
| 5,385,156 A | 1/1995 | Oliva |
| 5,411,481 A | 5/1995 | Allen et al. |
| 5,413,584 A | 5/1995 | Schulze |
| 5,417,699 A | 5/1995 | Klein et al. |
| 5,425,744 A | 6/1995 | Fagan et al. ................. 606/213 |
| 5,433,727 A | 7/1995 | Sideris |
| 5,451,235 A | 9/1995 | Lock et al. ................... 606/213 |
| 5,478,353 A | 12/1995 | Yoon |
| 5,480,424 A | 1/1996 | Cox |
| 5,486,193 A | 1/1996 | Bourne et al. ............... 606/194 |
| 5,507,811 A | 4/1996 | Koike et al. |
| 5,540,712 A | 7/1996 | Kleshinski et al. |
| 5,545,138 A | 8/1996 | Fugoso et al. |
| 5,571,135 A | 11/1996 | Fraser et al. |
| 5,573,542 A | 11/1996 | Stevens |
| 5,601,571 A | 2/1997 | Moss |
| 5,618,311 A | 4/1997 | Gryskiewicz |
| 5,620,461 A | 4/1997 | Muijs Van De Moer et al. |
| 5,626,599 A | 5/1997 | Bourne et al. ............... 606/194 |
| 5,634,936 A | 6/1997 | Linden et al. |
| 5,649,950 A | 7/1997 | Bourne et al. ............... 606/194 |
| 5,653,684 A | 8/1997 | Laptewicz et al. |
| 5,662,703 A | 9/1997 | Yurek et al. |
| 5,681,324 A | 10/1997 | Kammerer et al. |
| 5,683,411 A | 11/1997 | Kavteladze et al. |
| 5,693,085 A | 12/1997 | Buirge et al. |
| 5,702,421 A | 12/1997 | Schneidt |
| 5,709,707 A | 1/1998 | Lock et al. ................... 606/213 |
| 5,720,754 A | 2/1998 | Middleman et al. |
| 5,725,552 A | 3/1998 | Kotula et al. |
| 5,733,294 A | 3/1998 | Forber et al. |
| 5,733,337 A | 3/1998 | Carr, Jr. et al. ................. 623/11 |
| 5,741,297 A | 4/1998 | Simon |
| 5,776,162 A | 7/1998 | Kleshinski |
| 5,797,960 A | 8/1998 | Stevens et al. |
| 5,800,516 A | 9/1998 | Fine et al. |
| 5,807,384 A | 9/1998 | Mueller |
| 5,810,884 A | 9/1998 | Kim |
| 5,823,956 A | 10/1998 | Roth et al. |
| 5,829,447 A | 11/1998 | Stevens et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,879,366 A | 3/1999 | Shaw et al. |
| 5,893,856 A | 4/1999 | Jacob et al. |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stevens et al. |
| 5,928,250 A | 7/1999 | Koike et al. |
| 5,944,738 A | 8/1999 | Amplatz et al. |
| 5,948,427 A | 9/1999 | Yamamoto et al. |
| 5,955,110 A | 9/1999 | Patel et al. |
| 5,976,174 A | 11/1999 | Ruiz |
| 5,989,268 A | 11/1999 | Pugsley, Jr. et al. |
| 5,993,475 A | 11/1999 | Lin et al. |
| 5,993,844 A | 11/1999 | Abraham et al. ............. 424/423 |
| 5,997,575 A | 12/1999 | Whitson et al. |
| 6,010,517 A | 1/2000 | Baccaro |
| 6,024,756 A | 2/2000 | Huebsch et al. |
| 6,030,405 A | 2/2000 | Zarbatany et al. |
| 6,039,721 A | 3/2000 | Johnson et al. |
| 6,056,760 A | 5/2000 | Koike et al. |
| 6,077,291 A | 6/2000 | Das |
| 6,079,414 A | 6/2000 | Roth |
| 6,080,182 A | 6/2000 | Shaw et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,156,055 A | 12/2000 | Ravenscroft |
| 6,165,183 A | 12/2000 | Kuehn et al. |
| 6,165,204 A | 12/2000 | Levinson et al. |
| 6,171,329 B1 | 1/2001 | Shaw et al. |
| 6,174,322 B1 | 1/2001 | Schneidt |
| 6,187,016 B1 | 2/2001 | Hedges et al. |
| 6,187,039 B1 | 2/2001 | Hiles et al. |
| 6,190,353 B1 | 2/2001 | Makower et al. |
| 6,200,313 B1 | 3/2001 | Abe et al. |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,265,333 B1 | 7/2001 | Dzenis et al. |
| 6,270,515 B1 | 8/2001 | Linden et al. |
| 6,277,138 B1 | 8/2001 | Levinson et al. |
| 6,287,317 B1 | 9/2001 | Makower et al. |
| 6,290,674 B1 | 9/2001 | Roue et al. |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,446 B1 | 11/2001 | Huebsch et al. |
| 6,315,791 B1 | 11/2001 | Gingras et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. ................. 623/1.38 |
| 6,342,064 B1 | 1/2002 | Koike et al. |
| 6,344,049 B1 | 2/2002 | Levinson et al. |
| 6,346,074 B1 | 2/2002 | Roth |
| 6,348,041 B1 | 2/2002 | Klint |
| 6,352,552 B1 | 3/2002 | Levinson et al. |
| 6,355,052 B1 | 3/2002 | Neuss et al. |

| | | |
|---|---|---|
| 6,364,853 B1 | 4/2002 | French et al. |
| 6,369,039 B1 | 4/2002 | Palasis et al. |
| 6,375,625 B1 | 4/2002 | French et al. |
| 6,375,671 B1 | 4/2002 | Kobayashi et al. |
| 6,379,342 B1 | 4/2002 | Levinson |
| 6,379,368 B1 | 4/2002 | Corcoran et al. |
| 6,387,104 B1 | 5/2002 | Pugsley, Jr. et al. |
| 6,391,048 B1 | 5/2002 | Ginn et al. |
| 6,398,796 B2 | 6/2002 | Levinson |
| 6,402,772 B1 | 6/2002 | Amplatz et al. |
| 6,419,669 B1 | 7/2002 | Frazier et al. |
| 6,436,088 B2 | 8/2002 | Frazier et al. |
| 6,440,152 B1 | 8/2002 | Gainor et al. |
| 6,460,749 B1 | 10/2002 | Levinson et al. |
| 6,482,224 B1 | 11/2002 | Michler et al. |
| 6,488,706 B1 | 12/2002 | Solymar |
| 6,494,888 B1 | 12/2002 | Laufer et al. |
| 6,517,550 B1 | 2/2003 | Konya et al. |
| 6,551,303 B1 | 4/2003 | Van Tassel et al. |
| 6,551,344 B2 | 4/2003 | Thill |
| 6,569,181 B1 | 5/2003 | Burns et al. |
| 6,596,013 B2 | 7/2003 | Yang et al. |
| 6,608,040 B1 | 8/2003 | Lin et al. |
| 6,623,508 B2 | 9/2003 | Shaw et al. |
| 6,623,518 B2 | 9/2003 | Thompson et al. |
| 6,666,861 B1 | 12/2003 | Grabek |
| 6,712,836 B1 | 3/2004 | Berg et al. |
| 6,726,696 B1 | 4/2004 | Houser et al. |
| 6,866,679 B2 | 3/2005 | Kusleika |
| 6,939,348 B2 | 9/2005 | Malecki et al. |
| 7,153,320 B2 | 12/2006 | Euteneuer et al. |
| 7,165,552 B2 | 1/2007 | Deem et al. |
| 2001/0014800 A1 | 8/2001 | Frazier et al. |
| 2001/0034537 A1 | 10/2001 | Shaw et al. |
| 2001/0037129 A1 | 11/2001 | Thill |
| 2001/0039435 A1 | 11/2001 | Roue et al. |
| 2001/0041914 A1 | 11/2001 | Roue et al. |
| 2001/0041915 A1 | 11/2001 | Frazier et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0026208 A1 | 2/2002 | Roe et al. |
| 2002/0029048 A1 | 3/2002 | Miller |
| 2002/0032462 A1 | 3/2002 | Houser et al. |
| 2002/0035374 A1 | 3/2002 | Borillo et al. |
| 2002/0043307 A1 | 4/2002 | Ishida et al. |
| 2002/0052572 A1 | 5/2002 | Franco et al. |
| 2002/0055767 A1 | 5/2002 | Forde |
| 2002/0077555 A1 | 6/2002 | Schwartz |
| 2002/0084178 A1 | 7/2002 | Dubson et al. |
| 2002/0096183 A1 | 7/2002 | Stevens et al. |
| 2002/0099389 A1 | 7/2002 | Michler et al. |
| 2002/0107531 A1 | 8/2002 | Schreck et al. |
| 2002/0111637 A1 | 8/2002 | Kaplan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0161427 A1 | 10/2002 | Rabkin |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2003/0028213 A1 | 2/2003 | Thill et al. |
| 2003/0045893 A1 | 3/2003 | Ginn |
| 2003/0050665 A1 | 3/2003 | Ginn |
| 2003/0059640 A1 | 3/2003 | Marton et al. |
| 2003/0065379 A1 | 4/2003 | Babbs et al. .............. 623/1.13 |
| 2003/0073979 A1 | 4/2003 | Naimark et al. |
| 2003/0100920 A1 | 5/2003 | Akin et al. |
| 2003/0114879 A1 | 6/2003 | Euteneuer et al. |
| 2003/0139819 A1 | 7/2003 | Beer et al. .............. 623/23.71 |
| 2003/0191495 A1 | 10/2003 | Ryan et al. |
| 2003/0191526 A1 | 10/2003 | Van Tassel et al. |
| 2003/0195530 A1 | 10/2003 | Thill |
| 2003/0204203 A1 | 10/2003 | Khairkhahan et al. |
| 2003/0208232 A1* | 11/2003 | Blaeser et al. .............. 606/213 |
| 2004/0044361 A1 | 3/2004 | Frazier et al. |
| 2004/0073230 A1 | 4/2004 | Mulholland et al. |
| 2004/0143291 A1 | 7/2004 | Corcoran et al. |
| 2004/0181237 A1 | 9/2004 | Forde et al. |
| 2004/0210301 A1 | 10/2004 | Obermiller |
| 2004/0230185 A1 | 11/2004 | Malecki et al. |
| 2004/0243122 A1 | 12/2004 | Auth et al. |
| 2004/0267191 A1 | 12/2004 | Gifford, III et al. |
| 2005/0021016 A1 | 1/2005 | Malecki et al. |
| 2005/0080406 A1 | 4/2005 | Malecki et al. |
| 2005/0131401 A1 | 6/2005 | Malecki et al. |
| 2005/0131460 A1 | 6/2005 | Gifford, III et al. |
| 2006/0027241 A1 | 2/2006 | Malecki et al. |
| 2006/0074410 A1 | 4/2006 | Malecki et al. |
| 2006/0241581 A1 | 10/2006 | Malecki et al. |
| 2006/0241582 A1 | 10/2006 | Malecki et al. |
| 2006/0241583 A1 | 10/2006 | Malecki et al. |
| 2006/0241584 A1 | 10/2006 | Malecki et al. |
| 2006/0247612 A1 | 11/2006 | Malecki et al. |
| 2006/0271030 A1 | 11/2006 | Francis et al. |
| 2006/0271040 A1 | 11/2006 | Horne et al. |
| 2006/0271089 A1 | 11/2006 | Alejandro et al. |
| 2006/0276779 A1 | 12/2006 | Malecki et al. |
| 2006/0276846 A1 | 12/2006 | Malecki et al. |
| 2007/0010806 A1 | 1/2007 | Malecki et al. |

FOREIGN PATENT DOCUMENTS

| | | |
|---|---|---|
| EP | 1 222 897 A2 | 7/2002 |
| WO | WO 94/25099 | 11/1994 |
| WO | WO 96/25179 | 8/1996 |
| WO | WO 96/31157 | 10/1996 |
| WO | WO 98/07375 | 2/1998 |
| WO | WO 98/26738 | 6/1998 |
| WO | WO 99/05977 | 2/1999 |
| WO | WO 99/18862 | 4/1999 |
| WO | WO 99/18864 | 4/1999 |
| WO | WO 99/18870 | 4/1999 |
| WO | WO 99/18871 | 4/1999 |
| WO | WO 99/30640 | 6/1999 |
| WO | WO 00/27292 | 5/2000 |
| WO | WO 01/08600 | 2/2001 |
| WO | WO 01/21247 | 3/2001 |
| WO | WO 01/26702 | 4/2001 |
| WO | WO 01/30266 | 5/2001 |
| WO | WO 01/30267 | 5/2001 |
| WO | WO 01/30268 | 5/2001 |
| WO | WO 01/49185 | 7/2001 |
| WO | WO 01/78596 | 10/2001 |
| WO | WO 01/93783 | 12/2001 |
| WO | WO 02/17809 | 3/2002 |
| WO | WO 02/24106 | 3/2002 |
| WO | WO 03/022159 | 3/2003 |
| WO | WO 03/059152 | 7/2003 |
| WO | WO 03/061481 | 7/2003 |
| WO | WO 03/073944 | 9/2003 |
| WO | WO 03/077733 | 9/2003 |

OTHER PUBLICATIONS

Written Opinion of the International Searching Authority for International Application No. PCT/US2005/003126, mailed Sep. 30, 2005, (11 pages).

Kimura et al., "Effects of Neutron Irradiation on the Transformation Behavior in Ti—Ni Alloys," Abstract, Proceedings of the Int'l Conf. on Mariensitic Transformations (1992) 935-940.

National Aeronautics and Space Administration, "55-Nitinol-the Alloy with a Memory: Its Physical Mettallurgy, Properties, and Applications," A-Report, 24-25, 1972.

Patent Cooperation Treaty (PCT) International Search Report (PCT Article 18 and Rules 43 and 44), International Application No. PCT/US2004/019919, International Filing Date: Nov. 22, 2004, Applicant: NMT Medical, Inc.-

Patent Cooperation Treaty (PCT) Written Opinion of the International Searching Authority (PCT Rule 43bis.1), International Application No. PCT/US2004/019919, International Filing Date: Nov. 22, 2004, Applicant: NMT Medical, Inc.

Ramanathan et al., "Experimental and Computational Methods for Shape Memory Alloys," 15th ASCE Engineering Mechanics Conf. (Jun. 2-5, 2002) 12 pages.

Shabalovskaya, "Surface, Corrosion and Biocompatibility Aspects of Nitinol as an Implant Material," Bio-Medical Materials and Engineering, (2002) 12:69-109.

Stöckel, "Nitinol Medical Devices and Implants," *SMST-2000: Proceedings of the International Conference on Shape Memory and Suerelastic Technologies*, 531-540, 2001.

Uchil, "Shape Memory Alloys-Characterization Techniques," Pramana-Journal of Physics, (2002) 58(5-6):1131-1139.

\* cited by examiner

DEVICES, SYSTEMS AND METHODS FOR CLOSURE OF CARDIAC OPENINGS

CROSS REFERENCE TO RELATED APPLICATIONS

This application is a divisional application of prior U.S. patent application Ser. No. 11/045,026, filed on Jan. 27, 2005 now abandoned, the entire disclosure of which is incorporated by reference herein, and which incorporates by reference, and claims priority to and the benefit of, U.S. Provisional Patent Application Ser. Nos. 60/540,474, 60/540,827, and 60/540,821, each of which were filed on Jan. 30, 2004.

TECHNICAL FIELD

The invention generally relates to devices, systems, and related methods for closing cardiac openings. More particularly, the invention features devices, systems, and related methods for the percutaneous transluminal closure of patent foramen ovales and left atrial appendages.

BACKGROUND

The human heart is divided into four compartments or chambers. The left and right atria are located in the upper portion of the heart and the left and right ventricles are located in the lower portion of the heart. The left and right atria are separated from each other by a muscular wall, the intraatrial septum, while the ventricles are separated by the intraventricular septum.

Either congenitally or by acquisition, abnormal openings, holes, or shunts can occur between the chambers of the heart or the great vessels, causing blood to inappropriately flow therethrough. Such deformities are usually congenital and originate during fetal life when the heart forms from a folded tube into a four chambered, two-unit system. The septal deformities result from the incomplete formation of the septum, or muscular wall, between the chambers of the heart and can cause significant problems.

One such septal deformity or defect, a patent foramen ovale, is a persistent, one-way, usually flap-like opening in the wall between the right atrium and left atrium of the heart. Since left atrial pressure is normally higher than right atrial pressure, the flap typically stays closed. Under certain conditions, however, right atrial pressure exceeds left atrial pressure, creating the possibility for right to left shunting that can allow blood clots to enter the systemic circulation. This is particularly problematic for patients who are prone to forming venous thrombus, such as those with deep vein thrombosis or clotting abnormalities.

Moreover, certain patients are prone to atrial arrhythmias (i.e., abnormal heart rhythms which can cause the heart to pump less effectively). In a common such abnormality, atrial fibrillation, the two upper chambers of the heart (i.e., the left atria and the right atria), quiver instead of beating effectively. Because the atria do not beat and empty cleanly during atrial fibrillation, blood can stagnate on the walls and form clots that can then pass through the heart and into the brain, causing a stroke or a transient ischemic attack. These clots typically form in a cul-de-sac in the heart called the left atrial appendage due to its tendency to have low or stagnant flow.

Nonsurgical (i.e., percutaneous) closure of a patent foramen ovale and similar cardiac openings such as an atrial septal defect or a ventricular septal defect, and obliteration of a left atrial appendage can be achieved using a variety of mechanical closure devices. These closure devices typically consist of a metallic structural framework with a scaffold material attached thereto. Currently available closure devices, however, are often complex to manufacture, are inconsistent in performance, require a technically complex implantation procedure, lack anatomic conformability, and lead to complications (e.g., thrombus formation, chronic inflammation, residual leaks, perforations, fractures, and conduction system disturbances).

Improved devices, systems, and related methods for closing cardiac openings, such as, for example, a patent foramen ovale, and for obliterating cardiac cul-de-sacs, such as, for example, a left atrial appendage, are, therefore, needed.

SUMMARY OF THE INVENTION

The present invention provides devices, compounds, systems, and related methods for closing cardiac openings. A device of the invention may include, for example, a patch with an adhesive and/or a removable frame. The patch can be placed across a cardiac opening, such as a patent foramen ovale or a left atrial appendage, to substantially occlude the cardiac opening. Alternatively, in another aspect, the device includes a U-shaped patch, together with an adhesive, that is specifically configured for attachment to a septum secundum and closure of a patent foramen ovale.

Moreover, in another aspect, a compound may be used to assist the device in closing, or may be used on its own to close, a cardiac opening. For example, a compound that includes an adhesive and a plurality of composite particles disposed within the adhesive may be used in that regard. In one embodiment, the plurality of composite particles disposed within the adhesive expand upon contact with blood and/or water, thereby locking the compound into place in the cardiac opening to substantially occlude the cardiac opening.

In using the devices and compounds of the invention to close cardiac openings, the aforementioned disadvantages associated with the closure devices known in the art are minimized or eliminated.

In one aspect, the invention provides a closure device for percutaneous transvascular closure of a cardiac opening. The closure device includes a patch, an adhesive coated on the patch, and at least one hollow channel enclosed within the patch.

Various embodiments of this aspect of the invention include the following features. The patch may include a bioresorbable material and the adhesive may be a light activated adhesive, such as, for example, an adhesive curable with ultraviolet light. The hollow channel enclosed within the patch may, for its part, be a conduit for light. The closure device may further include a fiber optic cable, and/or a removable frame, enclosed within the hollow channel. In another embodiment, the closure device includes a divider that has first and second surfaces. The first surface is coupled to the adhesive and the second surface is coated with a primer.

In another aspect, the invention relates to a method for percutaneous transluminal closure of a cardiac opening in a patient. The method includes inserting a closure device as described above into a heart of the patient and positioning the closure device across the cardiac opening to substantially occlude the cardiac opening.

In various embodiments of this aspect of the invention, positioning the closure device across the cardiac opening includes coupling the closure device to a tissue surface of the patient proximate the cardiac opening. The cardiac opening may be, for example, a patent foramen ovale or a left atrial appendage. Coupling the closure device to the tissue surface may include providing light to the hollow channel enclosed within the patch and activating the adhesive coated on the patch with the provided light. In another embodiment, coupling the closure device to the tissue surface includes applying a primer to the tissue surface.

In yet another aspect, the invention provides a closure device for percutaneous transluminal closure of a cardiac opening. The closure device includes a patch, at least one hollow channel enclosed within the patch, and a removable frame enclosed within the hollow channel.

In one embodiment of this aspect of the invention, the patch is made from a collagen material. In another embodiment, the frame is constructed from a shape memory alloy, such as, for example, nitinol.

In still another aspect, the invention relates to a method for percutaneous transluminal closure of a cardiac opening in a patient. The method includes inserting a closure device as immediately described above into a heart of the patient and positioning the closure device across the cardiac opening to substantially occlude the cardiac opening.

In various embodiments of this aspect of the invention, positioning the closure device across the cardiac opening includes coupling the closure device to a tissue surface of the patient proximate the cardiac opening. The cardiac opening may be, for example, a patent foramen ovale or a left atrial appendage. In one embodiment, coupling the closure device to the tissue surface includes thermally welding the closure device to the tissue surface. In another embodiment, the frame of the closure device is removed from within the hollow channel after the closure device is thermally welded to the tissue surface.

In another aspect, the invention provides a closure device for percutaneous transluminal closure of a cardiac opening. The closure device includes a housing, a releasable patch coupled to the housing, and an adhesive coated on the releasable patch.

In one embodiment of this aspect of the invention, the housing is substantially conically shaped. In another embodiment, the releasable patch includes a bioresorbable material. The adhesive may be a light activated adhesive, such as, for example, an adhesive curable with ultraviolet light. In yet another embodiment, the closure device includes a light source enclosed within the housing. The light source may be, for example, a light bulb or a fiber optic cable. In still another embodiment, the closure device includes a divider that has first and second surfaces. The first surface is coupled to the adhesive and the second surface is coated with a primer.

In yet another aspect, the invention relates to a method for percutaneous transluminal closure of a cardiac opening in a patient. The method includes inserting a closure device as immediately described above into a heart of the patient and positioning the releasable patch of the closure device across the cardiac opening to substantially occlude the cardiac opening.

In various embodiments of this aspect of the invention, positioning the releasable patch of the closure device across the cardiac opening includes coupling the releasable patch to a tissue surface of the patient proximate the cardiac opening. The cardiac opening may be, for example, a patent foramen ovale or a left atrial appendage. Coupling the releasable patch of the closure device to the tissue surface may include providing a light source emitting light within the housing and activating the adhesive coated on the releasable patch with the emitted light. In another embodiment, coupling the releasable patch to the tissue surface includes applying a primer to the tissue surface. In yet another embodiment, coupling the releasable patch to the tissue surface includes separating the releasable patch from the housing.

Additionally, in another aspect, the invention provides a closure device for percutaneous transvascular closure of a patent foramen ovale. The closure device includes a U-shaped patch configured for attachment to a septum secundum and an adhesive coated on the U-shaped patch.

In one embodiment of this aspect of the invention, a substance for stimulating tissue in-growth into the closure device is coated on the U-shaped patch. The substance may be, for example, a growth factor, a pharmacological agent to stimulate tissue growth, an irritant to encourage an inflammatory response, cells, or genes. In another embodiment, a substance for increasing endothelization, or, alternatively, a substance for decreasing thrombogenicity, such as, for example, heparin, is coated on the U-shaped patch. In yet another embodiment, the closure device includes at least one barrier coupled to the U-shaped patch. The barrier may be a right atrial barrier for blocking an opening to the patent foramen ovale from the right atrium, or, alternatively, the barrier may be a left atrial barrier for blocking an opening to the patent foramen ovale from the left atrium.

The U-shaped patch may include a biological material, a bioresorable material, a synthetic material, a polymeric material, a shape memory material, and/or a metallic mesh material. The adhesive may be, for example, cyanoacrylate and/or a fibrin based adhesive.

In a further aspect, the invention provides a method for percutaneous transluminal closure of a patent foramen ovale in a patient. The method includes inserting a closure device into a heart of the patient and coupling the closure device to the septum secundum to substantially occlude the patent foramen ovale. The closure device includes a U-shaped patch configured for attachment to a septum secundum and an adhesive coated on the U-shaped patch.

In one embodiment of this aspect of the invention, coupling the closure device to the septum secundum includes gluing the closure device to the septum secundum.

In another aspect, the invention relates to a compound for percutaneous transluminal closure of a cardiac opening. The compound includes an adhesive and a plurality of composite particles disposed within the adhesive. The composite particles are capable of expansion upon contact with blood and/or water.

In various embodiments of this aspect of the invention, the adhesive is a fibrin based adhesive. The composite particles may be, for example, gelatin particles, biological particles, bioresorbable particles, and/or foam particles.

In yet another aspect, the invention provides a method for percutaneous transluminal closure of a cardiac opening in a patient. The method includes providing a compound as described above and injecting the compound into the cardiac opening to substantially occlude the cardiac opening.

In one embodiment of this aspect of the invention, the method further includes positioning a patch or a barrier across an end of the cardiac opening, which may be, for example, a patent foramen ovale or a left atrial appendage.

A device of the invention may further include specially designed balloons together with adhesives and/or substances for stimulating tissue growth coated on, or contained within, the specially designed balloons. According to one feature of the invention, the specially designed balloons ensure that the adhesives are only exposed once the balloons are located within the cardiac openings. Advantageously, the adhesives are exposed only to the tissue surface of the cardiac openings and not to a patient's blood prior to locating the balloons within the cardiac openings. By minimizing the exposure of the adhesives to blood, the risk of thrombus formation is reduced.

According to another feature of the invention, closure systems employ one or more locators for initially locating the cardiac openings and then properly positioning the balloons of the invention within the cardiac openings. Knowing that a balloon is properly positioned within a cardiac opening allows a physician to release the adhesive contained within the balloon at the appropriate time. As such, the risk of exposing the adhesive prior to locating the balloon within the cardiac opening, and the consequent risk of thrombus formation, is again reduced.

In one aspect, the invention provides a closure device for percutaneous transluminal closure of a cardiac opening. The closure device includes a balloon, which has an outer surface, and an adhesive. The balloon is inflatable between a deflated state and an inflated state. In the deflated state, the outer surface of the balloon involutes to form a cavity and the adhesive is coated on a surface of the cavity. In the inflated state, the cavity unfolds to form the outer surface of the balloon and the adhesive is coated on the outer surface of the balloon.

In one embodiment of this aspect of the invention, the cavity is formed around a mid-portion of the balloon, which may be tubularly-shaped. In another embodiment, the closure device further includes a substance for stimulating tissue growth. In the deflated state of the balloon, the growth substance is coated on the surface of the cavity. In the inflated state of the balloon, the growth substance is coated on the outer surface of the balloon.

In another aspect, the invention relates to a method for percutaneous transluminal closure of a cardiac opening in a patient. The method includes inserting a closure device as described above into a heart of the patient, positioning the closure device within the cardiac opening with the balloon of the closure device deflated, and inflating the balloon to expose the adhesive coated on the outer surface of the balloon to the cardiac opening. In one embodiment of this aspect of the invention, the balloon of the closure device is removed from the patient after the adhesive is exposed to the cardiac opening.

In yet another aspect, the invention provides a closure device that includes a balloon having an outer surface, a porous band encircling only a portion of the outer surface of the balloon, and an adhesive disposed between the outer surface of the balloon and the porous band. The porous band has a plurality of openings.

In one embodiment of this aspect of the invention, the porous band encircles a center portion of the balloon, which may be, for example, tubularly-shaped. In another embodiment, a substance for stimulating tissue growth is disposed between the outer surface of the balloon and the porous band.

In still another aspect, the invention relates to a method that includes inserting a closure device as just described into a heart of the patient, positioning the closure device within the cardiac opening, and applying a pressure to the balloon of the closure device to expose the adhesive through the plurality of openings of the porous band to the cardiac opening. In one embodiment of this aspect of the invention, the balloon and the porous band of the closure device are removed from the patient after the adhesive is exposed through the plurality of openings of the porous band to the cardiac opening.

Additionally, in another aspect, the closure device includes an outer balloon that has a plurality of first holes, an inner balloon that has a plurality of second holes, and an adhesive. The adhesive is contained within the inner balloon, which is itself contained within the outer balloon.

In various embodiments of this aspect of the invention, at least one of the plurality of first holes and the plurality of second holes includes pores. Alternatively, in another embodiment, at least one of the plurality of first holes and the plurality of second holes includes slits. In yet another embodiment, at least one of the inner balloon and the outer balloon is tubularly-shaped. In another embodiment, a substance for stimulating tissue growth is contained within the inner balloon.

In a further aspect, the invention relates to a method that includes inserting a closure device as just described into a heart of the patient, positioning the closure device within the cardiac opening, applying a first pressure to the inner balloon to express the adhesive through the plurality of second holes, and applying a second pressure to the outer balloon to express the adhesive through the plurality of first holes to the cardiac opening. In one embodiment of this aspect of the invention, the outer balloon and the inner balloon of the closure device are removed from the patient after the adhesive is expressed through the plurality of first holes to the cardiac opening.

In another aspect, the closure device includes a balloon and an adhesive. The balloon has a membrane constructed from a wicking material and the adhesive is contained within the membrane of the balloon.

In one embodiment of this aspect of the invention, the balloon is tubularly-shaped. In another embodiment, a substance for stimulating tissue growth is contained within the membrane of the balloon. At least a portion of the adhesive and/or the substance for stimulating tissue growth may be absorbed within the membrane of the balloon.

In yet another aspect, the invention relates to a method that includes inserting a closure device as just described into a heart of the patient, positioning the closure device within the cardiac opening, and contacting a tissue surface of the cardiac opening with the membrane of the balloon to apply the adhesive to the tissue surface of the cardiac opening. In one embodiment of this aspect of the invention, the balloon of the closure device is removed from the patient after the adhesive is applied to the tissue surface of the cardiac opening.

In various embodiments of the foregoing aspects of the invention, the adhesives are cyanoacrylates, fibrin based adhesives, albumin gluteraldehyde type adhesives, or light activated adhesives. Moreover, the substances for stimulating tissue growth may be, for example, growth factors, pharmacological agents for stimulating tissue growth, irritants for encouraging an inflammatory response, cells, or genes. The cardiac opening is, for example, a patent foramen ovale or a left atrial appendage.

In still another aspect, the invention relates to a method for percutaneous transluminal closure of a left atrial appendage in a patient. The method includes inserting a closure device into a heart of the patient and positioning the closure device within the left atrial appendage. The closure device includes a balloon having a plurality of holes and an adhesive contained within the balloon. The method further includes applying a pressure to the balloon to separate the plurality of holes and to expose the adhesive to the left atrial appendage. The method also includes coupling the balloon of the closure device to the left atrial appendage with the exposed adhesive.

Additionally, in another aspect, the invention provides a closure device that includes a balloon with an outer surface, a first adhesive coated on the outer surface of the balloon, and a light source located within the balloon.

In one embodiment of this aspect of the invention, the closure device further includes a second adhesive coated on an inner surface of the balloon. At least one of the first adhesive and the second adhesive may be a light activated adhesive. In another embodiment, the closure device further includes a divider having first and second surfaces. The first surface of the divider may be coupled to the first adhesive and the second surface of the divider may be coated with a primer. The balloon may be made of an elastomer, or, alternatively, a biological material, which may be, for example, a collagen or a bioresorbable polymer. The balloon may be tubularly-shaped.

In a further aspect, the invention relates to a method that includes inserting a closure device as just described into a heart of the patient, positioning the closure device within the cardiac opening, and coupling the closure device to the cardiac opening to substantially occlude the cardiac opening.

In various embodiments of this aspect of the invention, coupling the closure device to the cardiac opening includes inflating the balloon, emitting light from the light source located within the balloon, and activating the adhesive coated on the outer surface of the inflated balloon with the emitted light. The inflated balloon may then be deflated and left behind in the cardiac opening. Coupling the closure device to the cardiac opening may also include applying a primer to a tissue surface of the cardiac opening. The cardiac opening may be, for example, a patent foramen ovale or a left atrial appendage.

In another aspect, the invention provides a percutaneous transluminal system for positioning a closure device in a cardiac opening. The system includes a catheter, a closure device coupled to the catheter, and a first locator coupled to at least one of the catheter and the closure device. The first locator is for positioning the closure device within the cardiac opening.

In various embodiments of this aspect of the invention, the first locator is a disk, a plurality of arms, a rod, or a balloon. The first locator may be, for example, a right atrial locator or a left atrial locator. In one embodiment, an adhesive, such as, for example, a cyanoacrylate, a fibrin based adhesive, or an albumin gluteraldehyde type adhesive, is coated on the first locator. In another embodiment, the system further includes a second locator coupled to at least one of the catheter and the closure device. The second locator is also for positioning the closure device within the cardiac opening.

In one embodiment, the system further includes an adhesive coupled to the closure device. Again, the adhesive may be, for example, a cyanoacrylate, a fibrin based adhesive, or an albumin gluteraldehyde type adhesive. The adhesive coupled to the closure device may alternatively be a light activated adhesive and the system may further include a light source coupled to the catheter for activating the light activated adhesive.

In another embodiment, the closure device is a balloon, which may be, for example, tubularly-shaped. In one embodiment, the balloon includes a first end, a second end, and a lumen extending from the first end to the second end. In another embodiment, the balloon includes a first opening at the first end of the balloon and a second opening at the second end of the balloon. In yet another embodiment, the balloon comprises a plurality of holes. An adhesive may be coated on an outer surface of the balloon, coated on an inner surface of the balloon, or simply contained within the lumen of the balloon.

In still another aspect, the invention relates to a method for delivering a closure device to a cardiac opening in a patient. The method includes inserting, into a heart of the patient, a system for positioning the closure device within the cardiac opening. The system is as just described. The first locator of the system is used to locate the cardiac opening and also to position the closure device within the cardiac opening.

In various embodiments of this aspect of the invention, the method further includes coupling the closure device to the cardiac opening to substantially occlude the cardiac opening. The method may also include coupling the first locator to a tissue surface of the patient that is proximate the cardiac opening. The cardiac opening may be, for example, a patent foramen ovale or a left atrial appendage.

Additionally, in another aspect, the invention provides a percutaneous transluminal system for closing a cardiac opening. The system includes a first catheter having a proximal end, a distal end, and a lumen extending from the proximal end to the distal end, a second catheter at least partially enclosed within the lumen of the first catheter, and a lining coupled to the first and second catheters. The second catheter is movable between a retracted state and a deployed state. In the retracted state of the second catheter, the lining is positioned within the lumen of the first catheter. In the deployed state of the second catheter, the lining inverts and is positioned outside the lumen of the first catheter.

In various embodiments of this aspect of the invention, the lining is sock-shaped. Moreover, adhesives and/or substances for stimulating tissue growth, of the types described above, may be coated on a surface of the lining and/or contained within the lining itself.

In a further aspect, the invention relates to a method for percutaneous transluminal closure of a cardiac opening in a patient. The method includes inserting a system as just described into a heart of the patient, positioning the system proximate the cardiac opening with the second catheter in a retracted state, and deploying the second catheter to invert the lining and position the lining within the cardiac opening.

In one embodiment of this aspect of the invention, the system further includes an adhesive coated on a surface of the lining and the adhesive is exposed to the cardiac opening when the second catheter is deployed. In another embodiment, the lining includes a plurality of holes and the system further includes an adhesive contained within the lining. In such an embodiment, the adhesive is exposed through the plurality of holes to the cardiac opening when the second catheter is deployed. In yet another embodiment, the system is removed from the patient after the adhesive is exposed to the cardiac opening, which may be, for example, a patent foramen ovale.

The foregoing and other aspects, features, and advantages of the invention will become more apparent from the following description taken in conjunction with the accompanying drawings.

BRIEF DESCRIPTION OF THE DRAWING

In the drawings, like reference characters generally refer to the same parts throughout the different views. Also, the drawings are not necessarily to scale, emphasis instead generally being placed upon illustrating the principles of the invention.

DESCRIPTION

The present invention features devices, systems, and related methods for closing cardiac openings, such as, for example, the patent foramen ovale described below, and for obliterating cardiac cul-de-sacs, such as, for example, the left atrial appendage described below.

Figure 1:
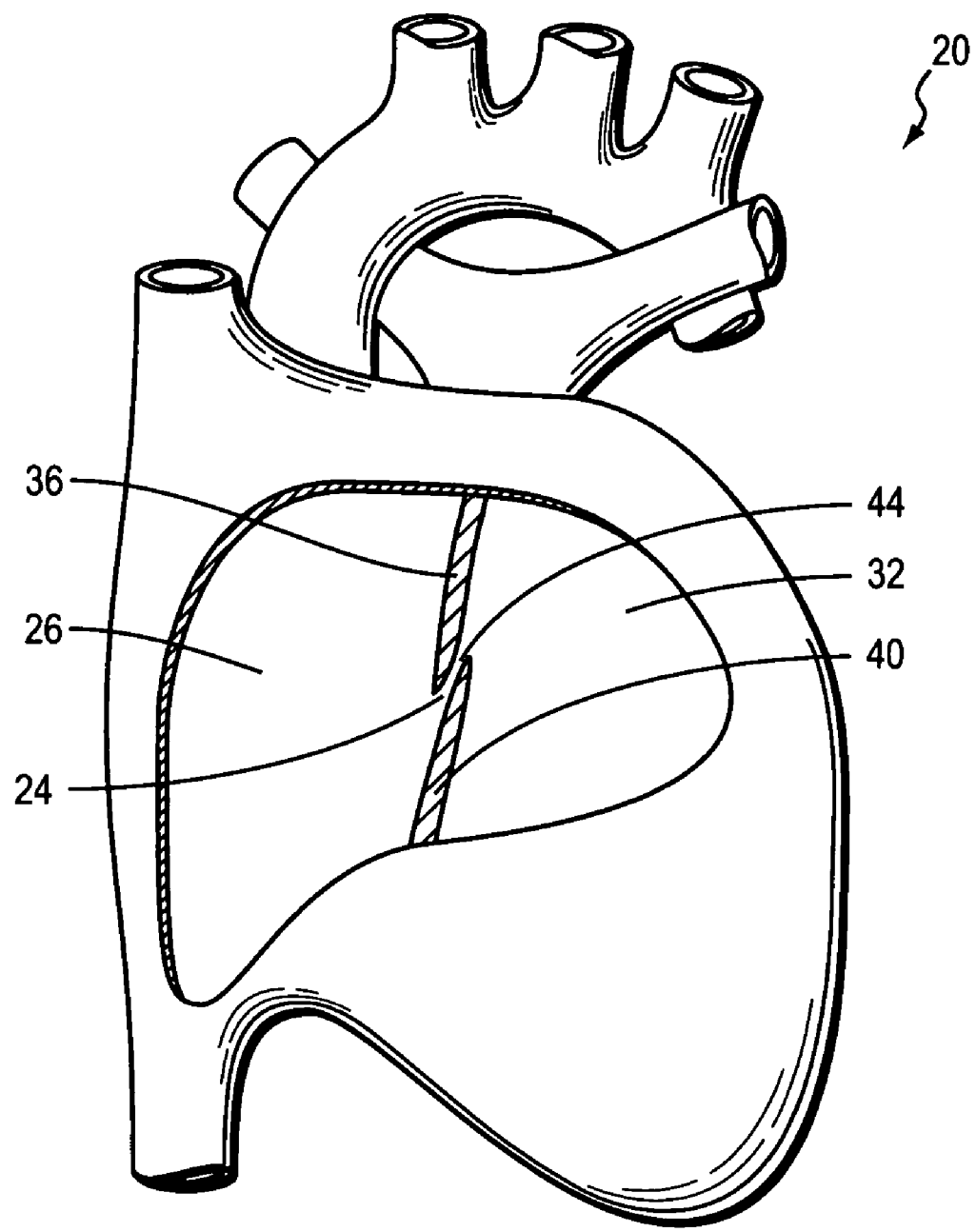
FIG. 1 is a cutaway view of a heart illustrating a patent foramen ovale.

FIG. 1 depicts a cutaway view of a heart 20. The heart 20 includes a septum 24 that divides a right atrium 26 from a left atrium 32. The septum 24 includes a septum secundum 36 and a septum primum 40. An exemplary cardiac opening, a patent foramen ovale 44, that is to be corrected by the devices, systems, and related methods of the present invention is located between the septum secundum 36 and the septum primum 40. The patent foramen ovale 44 provides an undesirable fluid communication between the right atrium 26 and the left atrium 32 and, under certain conditions, allows for the shunting of blood between the right atrium 26 and the left atrium 32. If the patent foramen ovale 44 is not closed or obstructed in some manner, a patient is placed at a higher risk for an embolic stroke in addition to other circulatory abnormalities.

Figure 2:
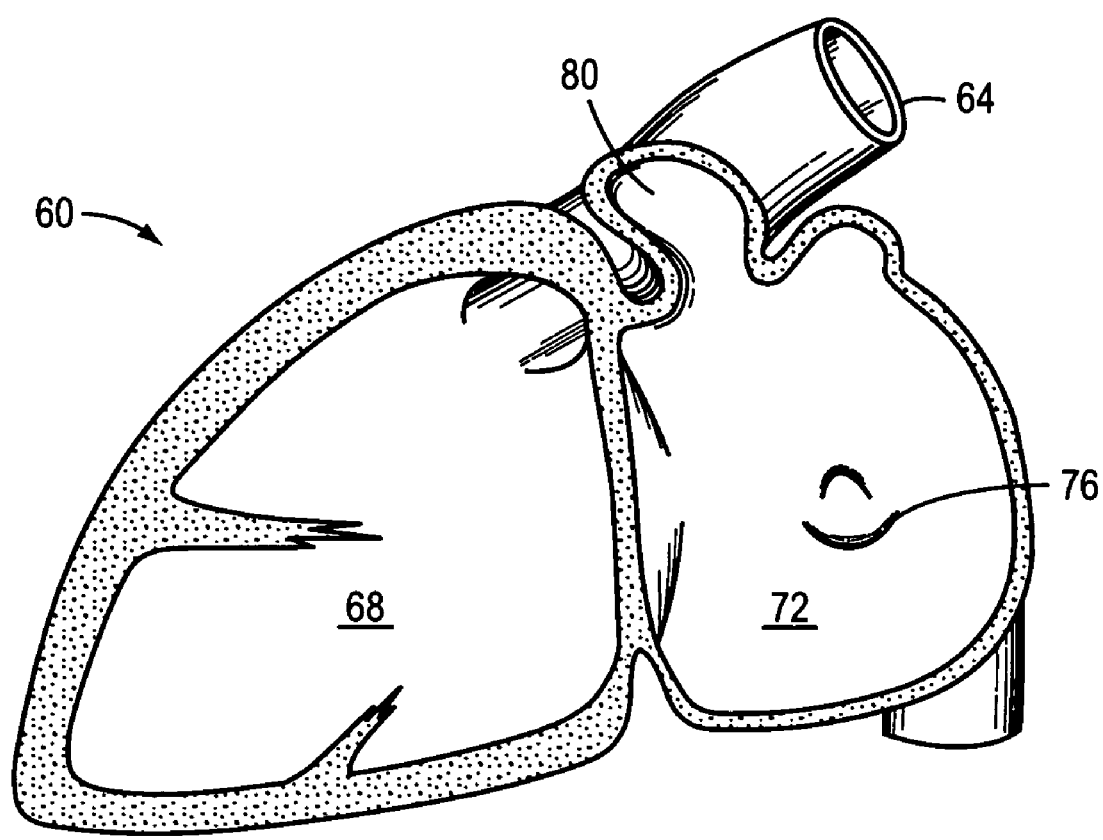
FIG. 2 is a partial cross-sectional view of another heart illustrating a left atrial appendage.

FIG. 2 depicts a partial cross-sectional view of another heart 60. The heart 60 includes an aorta 64, a left ventricle 68, a left atrium 72, and a fossa ovalis 76. The heart 60 also includes an exemplary cardiac cul-de-sac, a left atrial appendage 80, that is to be obliterated by the devices, systems, and related methods of the present invention. Under certain conditions, blood clots may form in the left atrial appendage 80. If the left atrial appendage 80 is not closed or obstructed in some manner, a patient is placed at a higher risk of having the blood clots pass from the heart 60 and into the vasculature of the brain, causing a stroke or a transient ischemic attack.

In broad overview, embodiments of the devices of the invention typically include a patch or a balloon. Referring to embodiments that include a patch, an adhesive may be coated on the patch and the adhesive may require activation (e.g., light activation) to bond the patch to a patient's tissue surface.

In one embodiment, to close a patient's cardiac opening, the patch is placed across the cardiac opening and the adhesive activated to bond the patch to the patient's tissue. The cardiac opening is thereby substantially occluded.

In another embodiment, a removable frame is enclosed within the patch. In one such embodiment, to substantially occlude the cardiac opening, the patch is placed across the cardiac opening and thermally welded to the patient's tissue. The frame is then removed from the patch.

In yet another embodiment, the patch is a U-shaped patch that is bonded to a septum secundum of a patent foramen ovale. The U-shaped patch includes, for example, a barrier that is attached to a septum primum to substantially occlude the patent foramen ovale. Alternatively, the U-shaped patch includes, for example, a substance that stimulates tissue growth from the septum secundum and/or the septum primum. In such a case, the patent foramen ovale is encouraged to heal itself.

Compounds of the invention may be employed on their own, or in conjunction with the devices of the invention, to occlude the cardiac openings described herein. Typically, the compounds are first physically injected or otherwise applied into the cardiac openings and thereafter expand to substantially occlude the cardiac openings.

Figure 3:
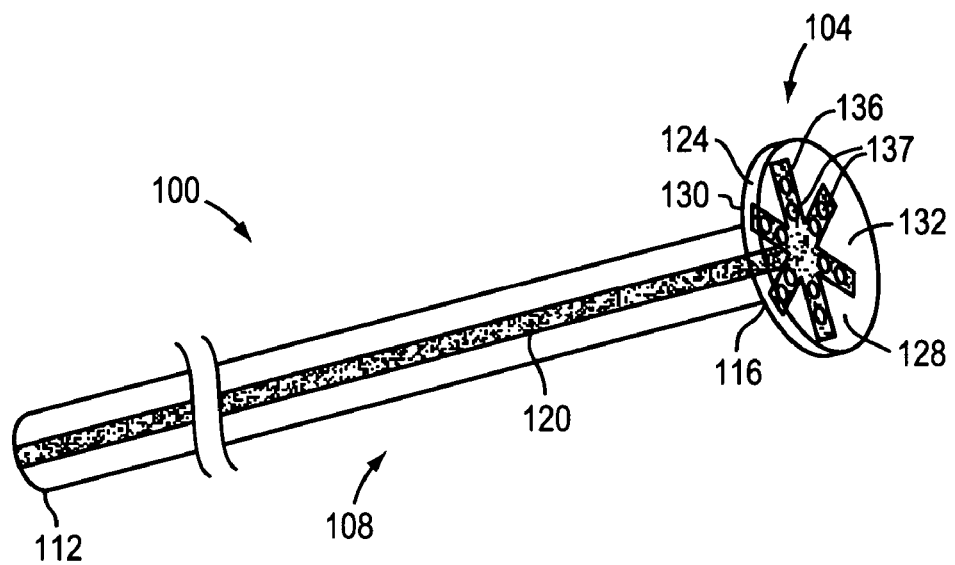
FIG. 3 is a schematic perspective view of a system, including a delivery catheter and a closure device, for the percutaneous transluminal closure of a cardiac opening according to an illustrative embodiment of the invention.

FIG. 3 depicts a system 100, capable of being used for the percutaneous transluminal closure of a cardiac opening, according to an illustrative embodiment of the invention. The system 100 includes a closure device 104 and a delivery catheter 108 that is used to deliver the closure device 104 to the cardiac opening in a patient's heart. In one embodiment, the delivery catheter 108 includes a proximal end 112 (i.e., an end that is closest to a physician when the physician is using the system 100), an opposite, distal end 116, and a lumen 120 that extends from the proximal end 112 to the distal end 116.

For its part, in one embodiment, the closure device 104 includes a patch 124 and at least one hollow channel 136 enclosed within the patch 124. For example, as illustrated, the patch 124 includes a plurality of hollow channels 136 extending from a common center similar to spokes of a wheel. The closure device 104 is coupled to the distal end 116 of the delivery catheter 108 such that the lumen 120 of the delivery catheter 108 is contiguous with the hollow channels 136 enclosed within patch 124. In one embodiment, the closure device 104 is releasably coupled to the distal end 116 of the delivery catheter 108. For example, the closure device 104 is coupled to the distal end 116 of the delivery catheter 108 so that it may be separated from the delivery catheter 108 through the application of a force, such as a torsional force applied by the physician to the proximal end 112 of the delivery catheter 108 and transmitted along the delivery catheter 108 to the point of coupling with the closure device 104.

The lumen 120 of the catheter 108 and the hollow channels 136 may be used, for example, as conduits to channel light through the delivery catheter 108 and the patch 124. In one embodiment, for example, a physician using the system 100 positions a light source (not shown) proximal to the proximal end 112 of the delivery catheter 108, or at some other point within the lumen 120 of the delivery catheter 108, and projects light down the lumen 120 and through the hollow channels 136 of the patch 124. Alternatively, in another embodiment, the lumen 120 and the hollow channels 136 enclose one or more fiber optic cables for delivering light through the delivery catheter 108 and the patch 124. In such a case, the fiber optic cables are connected at their proximal ends to a source of illumination. The light serves to activate adhesive 128 to bond the patch 124 to a patient's tissue.

Figure 4A:
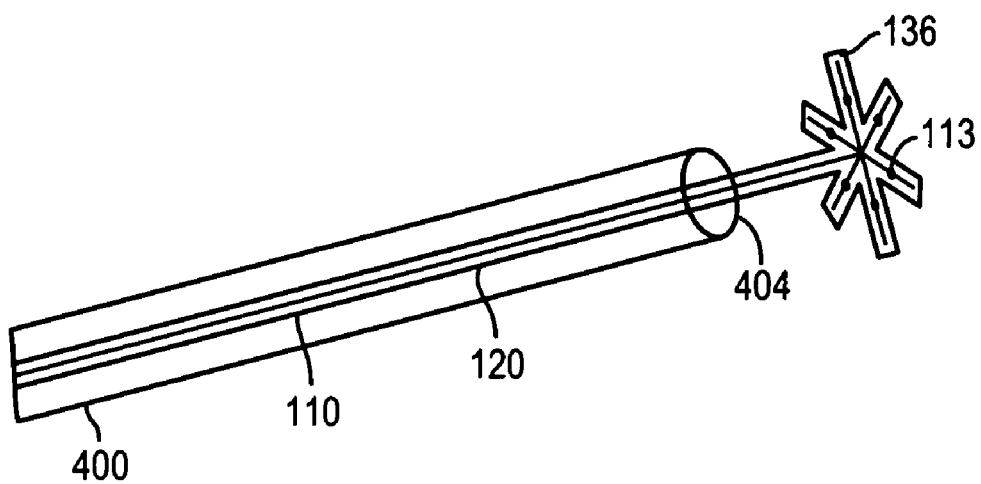
FIGS. 4A-4B illustrate extended and folded configurations of a frame for the closure device illustrated in FIG. 3, according to an illustrative embodiment of the invention.
Figure 4B:
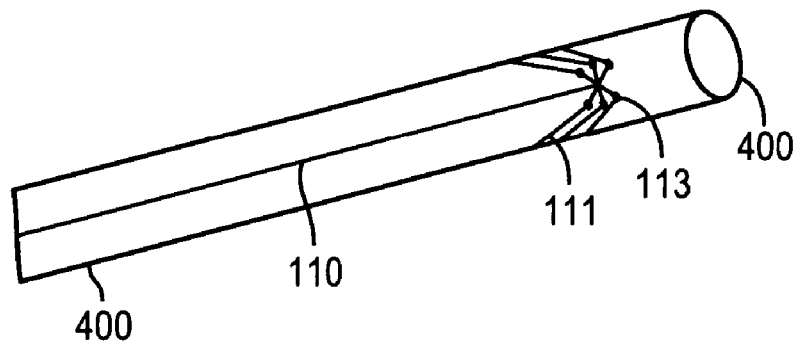

Referring to FIG. 4A, in yet another embodiment, the lumen 120 and the hollow channels 136 enclose a continuous frame 110. The frame 110 may be constructed from a shape memory alloy, such as, for example, from nitinol or, alternatively from a polymer, stainless steel, or any combination of the above materials. In one embodiment, the frame 110 is used as a means for expanding the patch 124 of the closure device 104 and as a means for holding the patch 124 flush against a patient's tissue surface proximate the cardiac opening. In a further embodiment, the frame 110 may include a plurality of arms having springs or resilient coils 113 that cause the closure device 104 to expand. Referring to FIG. 4B, in one embodiment, a physician advances a sheath 400 into a patient's heart and positions the distal end 404 of the sheath proximate the cardiac opening. This is described below with reference to FIGS. 11A and 11B. During advancement of the closure device 104 through the sheath 400, the arms 111 of frame 110 may bend at the springs or resilient coils 113 to facilitate passage of the closure device through the sheath 400. The frame 110 may also be coupled at its proximal end to a power supply and used to deliver radio frequency energy to a tissue surface proximate the cardiac opening.

In a particular embodiment, the fiber optic cables and/or the frame 110 may be removable from the patch 124 after the patch 124 is coupled to a patient's tissues proximate the cardiac opening. For example, the fiber optic cables and/or the frame 110 may be retracted from the hollow channels 136 of the patch 124 into the contiguous lumen 120 of the delivery catheter 108.

Referring again to FIG. 3, in one embodiment, an adhesive 128 is applied to the patch 124 as a coating. For example, the adhesive 128 is coated on a distal side 132 of the patch 124, or, alternatively, on a proximal side 130 of the patch 124 (not shown). The adhesive 128 may be, for example, a light activated adhesive, such as an adhesive curable with ultraviolet light. To bond the patch 124 to a patient's tissue surface proximate the cardiac opening, light may be delivered through the delivery catheter 108 and the patch 124 to the adhesive 128 and used to activate the adhesive 128.

Alternatively in still other embodiments, the adhesive 128 may be a heat activated adhesive, a chemically activated adhesive, or a bioreactive adhesive. In such alternative embodiments, the lumen 120 and hollow channels 136 are used to deliver heat, chemicals, or biological agents, respectively, to the adhesive 128. For example, the lumen 120 and hollow channels 136 may enclose a pipe to bidrectionally carry hot water proximate a heat activated adhesive 128. Alternatively, radio frequency energy (delivered, for example, by the frame 110 enclosed within the lumen 120 and the hollow channels 136), electrical resistance, ultrasound energy, laser energy, or chemical energy may be supplied to the heat activated adhesive 128.

In yet another embodiment, the adhesive 128, rather than being initially coated on the distal side 132 or on the proximal side 130 of the patch 124, is introduced to the distal side 132 or to the proximal side 130 of the patch 124 via the lumen 120 and the hollow channels 136. For example, in one embodiment illustrated in FIG. 3, holes 137, which pass from the hollow channels 136 to the surface of the patch 124, are present on the distal side 132 or on the proximal side 130 of the patch 124 in the region of the hollow channels 136. When the physician is ready to adhere the patch 124 to the patient's tissues proximate the intracardiac defect, the physician injects the adhesive 128 through the lumen 120, through the hollow channels 136, and through the holes 137 to the surface of the distal side 132 or the surface of the proximal side 130 of the patch 124.

In embodiments where the patch 124 includes the adhesive 128, the patch 124 may be made, either entirely or in part, from a biological material, a bioresorbable material (e.g., polylactide, glycolide, or caprolactone), a synthetic material (e.g., polyester, expanded polytetrafluoroethylene (ePTFE), or polyvinyl alcohol), a polymeric material, a shape memory material (e.g., a shape memory alloy), a metal mesh, or other suitable material for closing a cardiac opening, such as combinations of these materials. Moreover, portions of the patch 124 proximate the hollow channels 136 may be made from a translucent material.

In some embodiments, the closure device 104 is devoid of the adhesive 128. In such embodiments, radio frequency energy is delivered via the frame 110 and the patch 124 is thermally welded to a patient's tissue surface proximate the cardiac opening. In such embodiments, the patch 124 is typically made from a biological material. For example, the patch 124 is made from a collagen based material derived from the intestine, stomach, skin, bladder, or pericardium of a porcine animal, a bovine animal, and/or a human.

Referring still to FIG. 3, the patch 124 may be disk-shaped and have a circular cross-section. Alternatively, the patch 124 may have a variety of other cross-sectional shapes suitable for closing a cardiac opening, including, but not limited to, rectangular and triangular. The patch 124 may also include one or more radio-opaque markers or radio-opaque fillers to indicate its position within a patient's body.

Figure 5:
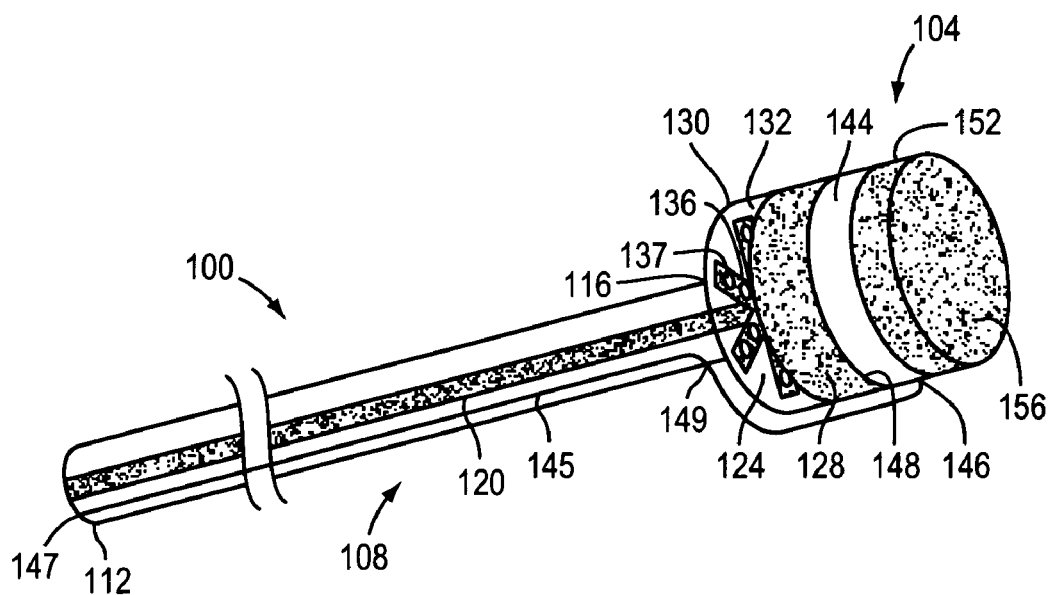
FIG. 5 is a schematic perspective view of a system, including a delivery catheter and a closure device, for the percutaneous transluminal closure of a cardiac opening according to another illustrative embodiment of the invention.

FIG. 5 depicts a system 100, capable of being used for the percutaneous transluminal closure of a cardiac opening, according to another illustrative embodiment of the invention. As shown, the closure device 104 of the system 100 further includes a removable divider 144, such as, for example, a non-reactive sheet 144, having a first surface 148 and a second surface 152. In the context of divider 144, non-reactive means that the divider does not appreciably adhere to adhesive 128, nor interact with material, such as a primer, that may be coated onto a surface of divider 144. The first surface 148 of the removable divider 144 contacts the adhesive 128 of the closure device 104. Coated on the second surface 152 of the removable divider 144 is a primer 156. In one embodiment, the primer 156 prepares the tissue surface of the patient to which the closure device 104 will be adhered during the process of closing the patient's cardiac opening. In another embodiment, the primer 156 helps to activate the adhesive 128 and/or bond the adhesive 128 to the patient's tissue surface. After application of the primer 156 to the tissue surface proximate the cardiac opening, the removable divider 144 may be removed from the rest of the closure device 104. In one embodiment, sutures 145, illustrated in FIG. 5, are attached to the removable divider 144 at a point 146 on the edge of the removable divider 144. The physician may remove the removable divider 144 from the rest of the closure device 104 by applying traction to the proximal end 147 of the suture, and withdrawing the removable divider 144 through a perforation 149 in the delivery catheter 108.

In one embodiment, illustrated in FIG. 5, the adhesive 128 is coated on a distal side 132 of the patch 124. The removable divider 144 and the primer 156 are therefore also located distal to the patch 124. Alternatively, in another embodiment, the adhesive 128 is coated on a proximal side 130 of the patch 124 (not shown). In such an embodiment, the removable divider 144 and the primer 156 are located proximal to the patch 124.

Figure 6:
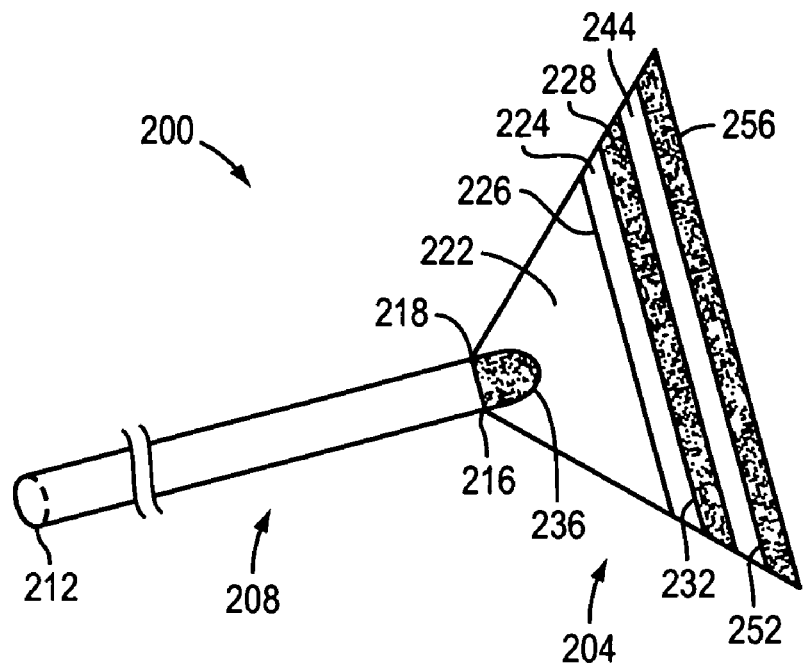
FIG. 6 is a schematic cross-sectional view of a system, including a delivery catheter and a closure device, for the percutaneous transluminal closure of a cardiac opening according to another illustrative embodiment of the invention.

FIG. 6 depicts a system 200, capable of being used for the percutaneous transluminal closure of a cardiac opening, according to another illustrative embodiment of the invention. The system 200 includes a closure device 204 and a delivery catheter 208 that is used to deliver the closure device 204 to the cardiac opening in a patient's heart. The delivery catheter 208 includes a proximal end 212 (i.e., an end that is closest to a physician when the physician is using the system 200) and an opposite, distal end 216. In one embodiment, the closure device 204 includes a housing 222, a releasable patch 224 coupled to a distal surface 226 of the housing 222, and an adhesive 228 coated on a distal side 232 of the releasable patch 224.

In one embodiment, as illustrated in FIG. 6, the housing 222 is conically shaped, with the distal surface 226 of the housing 222 forming the base of the cone and the apex 218 of the cone being coupled to the distal end 216 of the delivery catheter 208. Alternatively, the housing 222 may be otherwise shaped, for example as a tetrahedron with the distal surface 226 of the housing 222 forming the triangular base of the tetrahedron and the apex 218 of the tetrahedron being coupled to the distal end 216 of the delivery catheter 208. Enclosed within the housing 222 is, in one embodiment, a light source 236. The light source 236 may be, for example, a light bulb or a fiber optic cable that is used to deliver light to, for example, a light activated adhesive 228 located at the distal surface 226 of the housing 222.

As described above for the closure device 104, the releasable patch 224 of the closure device 204 may be made, either entirely or in part, from biological materials, bioresorbable materials, synthetic materials, polymeric materials, shape memory materials, and/or metal meshes. Moreover, portions of the releasable patch 224 may be made from a translucent material and may include one or more radio-opaque markers or radio-opaque fillers to indicate the anatomical position of the releasable patch 224 within a patient's body.

Referring still to FIG. 6, the releasable patch 224 of the closure device 204 may be disk-shaped and have a circular cross-section to match the shape of the distal surface 226 of the housing 222. Alternatively, the releasable patch 224 may have a variety of other cross-sectional shapes suitable for closing a cardiac opening. Where, for example, the housing 222 is shaped as a triangular prism, the releasable patch 224 may have a triangular or rectangular cross-section to match the shape of the distal surface 226 of the housing 222.

In one embodiment according to the invention, the adhesive 228, coated on the distal side 232 of the releasable patch 224, is a light activated adhesive. For example, the adhesive 228 is an adhesive curable with ultraviolet light. Alternatively, in other embodiments, the adhesive 228 may be a heat activated adhesive, a chemically activated adhesive, or a bioreactive adhesive. In such alternative embodiments, the light source 236 is replaced by other devices. For example, to deliver heat to a heat activated adhesive 228, a pipe may be used to bidirectionally carry hot water proximate the heat activated adhesive 228. Alternatively, electrical resistance, radio frequency energy, ultrasound energy, laser energy, or chemical energy is delivered to a heat activated adhesive 228. In still other embodiments, chemicals are delivered to a chemically activated adhesive 228 or biological agents are delivered to a bioreactive adhesive 228.

As described above with respect to FIG. 5 for the closure device 104, the closure device 204 may similarly further include a removable divider 244 having a primer 256 coated on its second surface 252. As illustrated in FIG. 6, the removable divider 244 separates the adhesive 228 from the primer 256.

Figure 7:
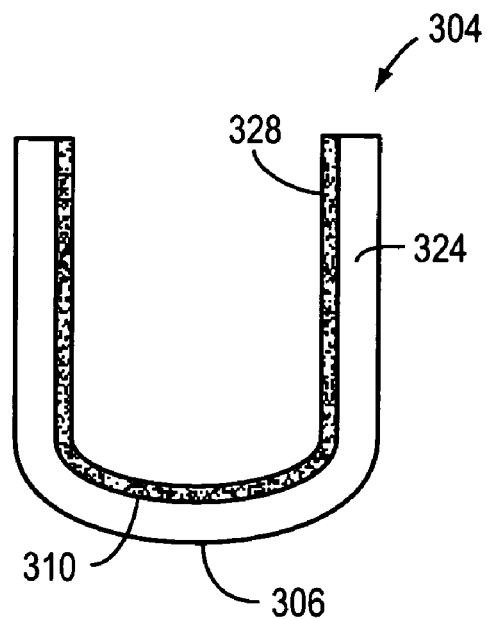
FIG. 7 is a schematic side view of a closure device for the percutaneous transluminal closure of a cardiac opening according to another illustrative embodiment of the invention.

FIG. 7 depicts a closure device 304, capable of being used for the percutaneous transluminal closure of a patent foramen ovale, according to another illustrative embodiment of the invention. As illustrated, the exemplary closure device 304 includes a U-shaped patch 324 and an adhesive 328. In one embodiment, the U-shaped patch 324 includes an outer surface 306 and an inner surface 310 to which the adhesive 328 is coated. The U-shaped patch is specifically configured for attachment to a septum secundum 36 of a patent foramen ovale.

The U-shaped patch 324 may be made from the biological materials, the bioresorbable materials, the synthetic materials, the polymeric materials, the shape memory materials, and/or the metal meshes described above, or from other suitable materials for closing a patent foramen ovale, such as combinations of these materials. For its part, the adhesive 328 may be, for example, a cyanoacrylate, a fibrin based adhesive, and/or a light activated adhesive.

In one embodiment, the U-shaped patch 324 further includes on its outer surface 306, i.e., convex surface, and/or on its inner surface 310, i.e., concave surface, a substance that stimulates in-growth of the patient's tissue into the patent foramen ovale following placement of the closure device 304 on the septum secundum 36 of the patent foramen ovale. In one embodiment, the growth substance is, for example, a growth factor, such as a vascular endothelial growth factor, a basic fibro growth factor, or an angiogenic growth factor. In another embodiment, the growth substance is a pharmacological agent for stimulating tissue growth, such as, for example, growth of cells or expression of genes. Alternatively, in another embodiment, the growth substance is a topical irritant for encouraging an inflammatory response, such as, for example, cotton seed oil or alcohol.

In one embodiment, because the closure device 304 is placed on the septum secundum 36, the growth substance is delivered to, or impregnated within, the septum secundum 36 and the tissue in-growth into the patent foramen ovale therefore occurs from the septum secundum 36. In another embodiment, the natural hydraulic pressure difference between the right atrium 26 and the left atrium 32 eventually causes the septum primum 40 to contact the closure device 304 that has been coupled to the septum secundum 36. In such a case, the growth substance coated on the outer surface 306 of the closure device 304 would contact the septum primum 40 and be delivered to, or impregnated within, the septum primum 40. Tissue in-growth into the patent foramen ovale would therefore occur from the septum primum 40. The newly grown tissue leads to the closure of the patent foramen ovale.

In yet another embodiment, a substance for increasing endothelization, or, alternatively, a substance for decreasing thrombogenicity, such as, for example, heparin, is coated on the outer surface 306 and/or on the inner surface 310 of the U-shaped patch 324.

Figure 8:
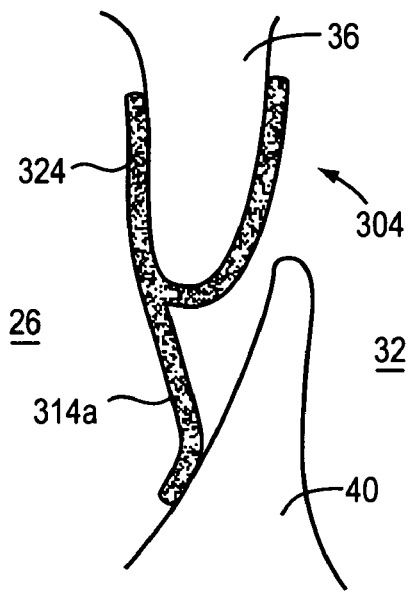
FIG. 8 is a schematic side view of a closure device, according to another illustrative embodiment of the invention, coupled to the septum secundum and the septum primum of a patent foramen ovale.
Figure 9:
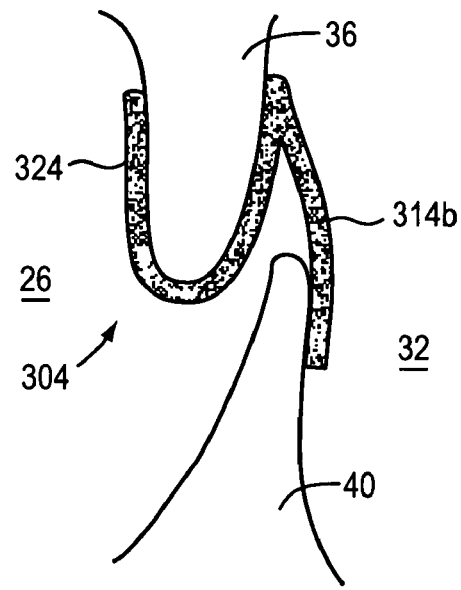
FIG. 9 is a schematic side view of a closure device, according to another illustrative embodiment of the invention, coupled to the septum secundum and the septum primum of a patent foramen ovale.
Figure 10:
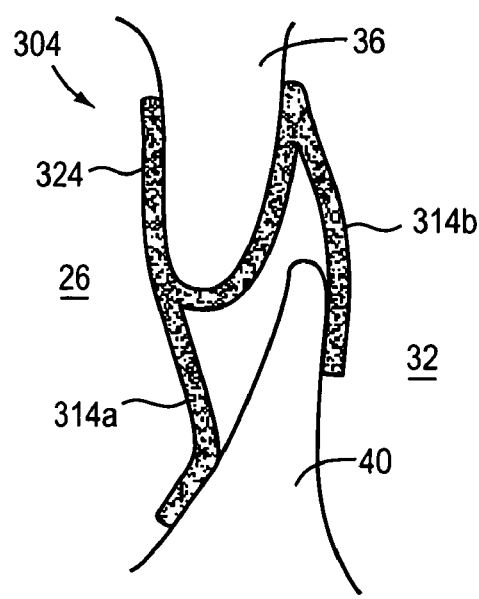
FIG. 10 is a schematic side view of a closure device, according to another illustrative embodiment of the invention, coupled to the septum secundum and the septum primum of a patent foramen ovale.

FIGS. 8, 9, and 10 depict, according to further illustrative embodiments of the invention, the exemplary closure device 304 of FIG. 7 coupled to the septum secundum 36 of a patent foramen ovale. As shown in each of FIGS. 8, 9, and 10, the closure device 304 may further include at least one barrier 314 coupled to the U-shaped patch 324. For example, the closure device 304 may include a right atrial barrier 314A, as shown in FIG. 8, for blocking an opening to the patent foramen ovale from the right atrium 26, a left atrial barrier 314B, as shown in FIG. 9, for blocking an opening to the patent foramen ovale from the left atrium 32, or, alternatively, both a right atrial barrier 314A and a left atrial barrier 314B, as shown in FIG. 10. In one embodiment, the right atrial barrier 314A and/or the left atrial barrier 314B include(s) an adhesive for bonding the barrier 314 to the septum primum 40, as shown. In another embodiment, the right atrial barrier 314A and/or the left atrial barrier 314B include(s), as described above for the U-shaped patch 324, a substance that stimulates tissue in-growth into the closure device 304 following placement of the closure device 304 on the septum secundum 36 of the patent foramen ovale.

Figure 11A:
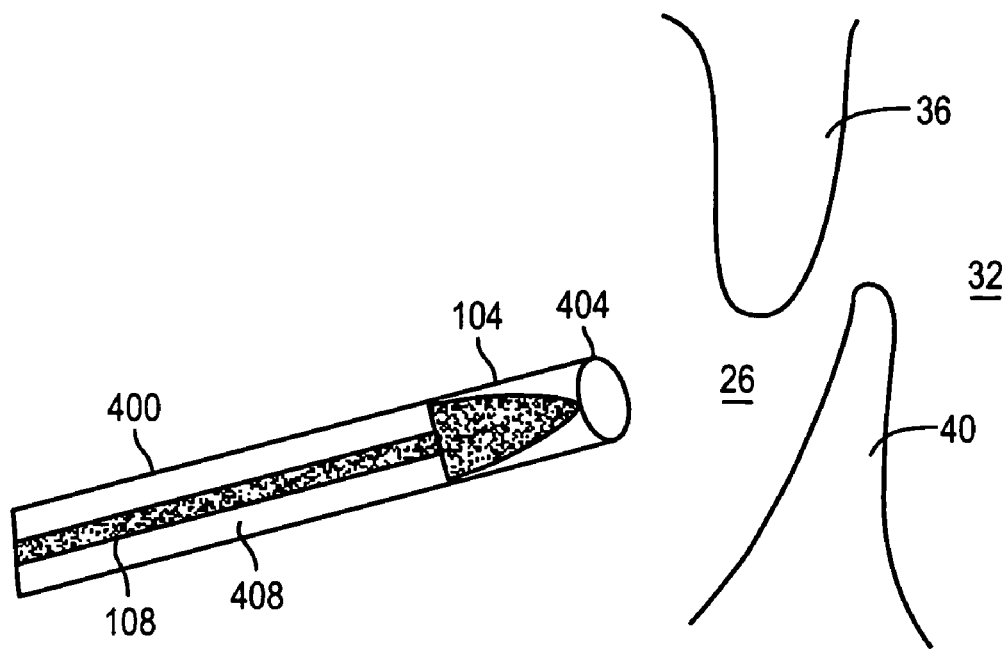
FIGS. 11A-11C illustrate the stages, according to an illustrative embodiment of the invention, for closing a patent foramen ovale in a patient.
Figure 11B:
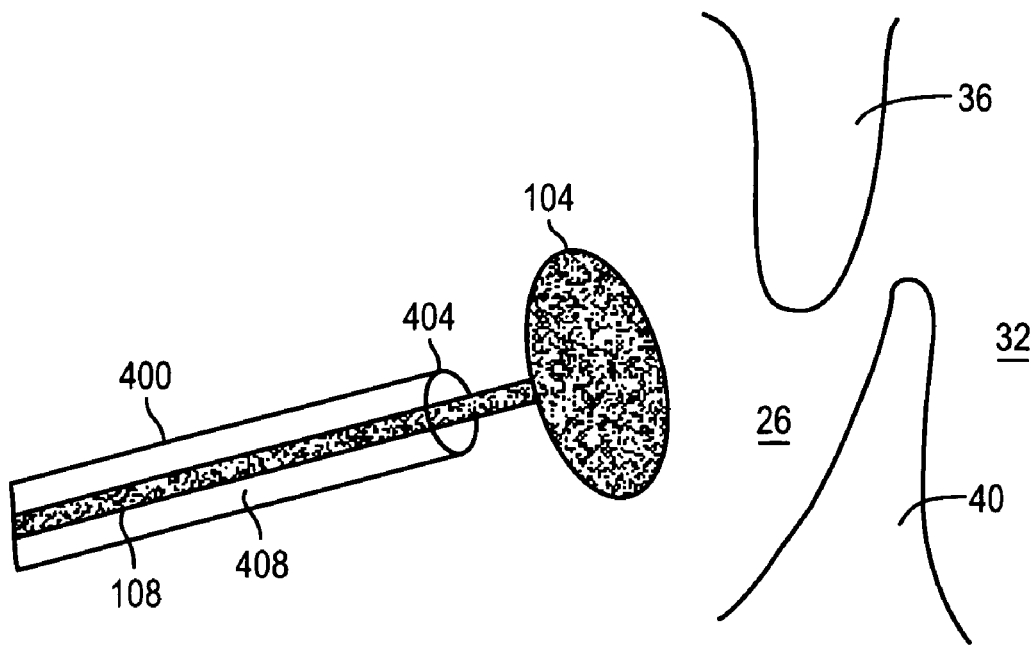
Figure 11C:
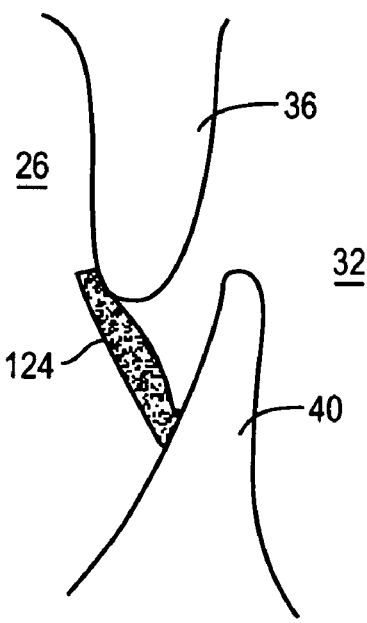

In another aspect, the invention provides methods for percutaneously closing a cardiac opening in a patient. FIGS. 11A-11C depict the steps of an illustrative method for closing a cardiac opening in a patient using the closure device 104 of the invention. Similar steps, with appropriate differences described below, are also performed in closing a cardiac opening in a patient using the closure device 204 of the invention. The cardiac opening illustrated in FIGS. 11A-11C is a patent foramen ovale. However, as described below, the methods of the invention may also be used to close or obliterate a left atrial appendage.

Referring to FIG. 11A, in one embodiment, an operator such as a physician advances a sheath 400 into the patient's heart and positions a distal end 404 of the sheath 400 proximate the cardiac opening. The physician then advances the system 100, including the closure device 104 and the delivery catheter 108, into and through a lumen 408 of the sheath 400. The physician continues to advance the system 100 though the lumen 408 of the sheath 400 until the closure device 104 exits the distal end 404 of the sheath 400 and expands to a position proximate the cardiac opening, as illustrated in FIG. 11B. The closure device 104 may be made to expand by any of a variety of means. For example, the shape memory frame 110 described above may cause the closure device 104 to expand. Alternatively, the patch 124 of the closure 104 may itself be made from a shape memory material, such as a shape memory alloy.

Where the closure device 104 includes both the adhesive 128 and the removable divider 144 containing the primer 156 (see FIG. 5), in order to couple the closure device 104 to a tissue surface of the patient proximate the cardiac opening, the physician first applies the primer 156 to the tissue surface. In one embodiment, the physician advances the closure device 104 distally to contact the patient's tissue surface with the primer 156 contained on the second surface 152 of the removable divider 144. The physician then withdraws the closure device 104 proximally to separate it from the patient's tissues and removes the removable divider 144 from about the rest of the closure device 104.

After applying the primer 156 to the patient's tissues proximate the cardiac opening and removing the removable divider 144, the physician advances the closure device 104 to contact the patient's tissue proximate the cardiac opening with the distal side 132 of the patch 124. In one embodiment, the adhesive 128 is coated on the surface of the distal side 132 of patch 124 and is therefore immediately applied to the patient's tissues. In another embodiment, after contacting the patient's tissues with the distal side 132 of the patch 124, the physician injects the adhesive 128 through the lumen 120, through the hollow channels 136, and through holes 137 on the distal side 132 of the patch 124 to apply the adhesive 128 to the patient's tissue.

With the adhesive 128 of the closure device 104 in contact with the patient's tissues proximate the cardiac opening, the physician activates the adhesive 128 to cure the adhesive 128 to the patient's tissues. Specifically, for a light activated adhesive 128, the physician provides light to the hollow channels 136 enclosed within the patch 124, thereby activating the adhesive 128. In another embodiment, where the physician uses the closure device 204 to close the cardiac opening (see FIG. 6), the physician causes the light source 236 enclosed within the housing 222 of the closure device 204 to emit light. The housing 222 prevents the blood in the area surrounding the closure device 204 from blocking, or otherwise interfering with, the passage of emitted light. The housing 222 therefore ensures that the emitted light reaches the adhesive 228 to activate the adhesive 228.

Figure 11D:
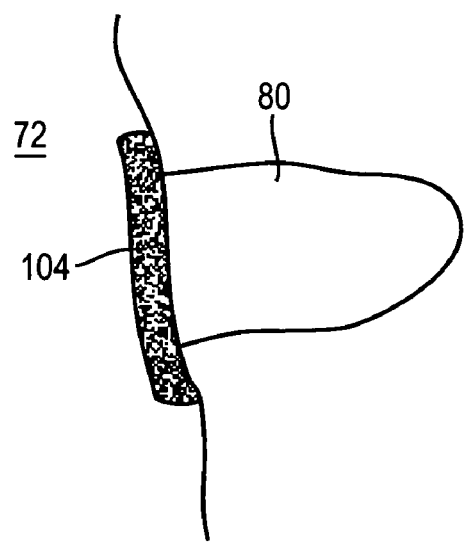
FIG. 11D illustrates a left atrial appendage closed according to an illustrative embodiment of the invention.

Once the adhesive 128 has cured to the patient's tissue proximate the cardiac opening, the physician separates the patch 124 of the closure device 104 from the delivery catheter 108 of the system 100, or, alternatively, separates the releasable patch 224 of the closure device 204 from the housing 222 of the closure device 204. For example, the physician causes the patch 124 or the releasable patch 224 to break away from the delivery catheter 108 or the housing 222, respectively, by applying a torque. Alternatively, a variety of other mechanical means may be used to separate the patch 124 from the delivery catheter 108 or the releasable patch 224 from the housing 222. Accordingly, the patch 124 of the closure device 104, or the releasable patch 224 of the closure device 204, is positioned across the cardiac opening to substantially occlude the cardiac opening. For instance, as illustrated in FIG. 11C, the patch 124 is positioned across a patent foramen ovale. In another embodiment, steps similar to those described above are performed to position the patch across a left atrial appendage 80, as illustrated in FIG. 11D.

Alternatively, in another embodiment, as described above, the hollow channels 136 of the patch 124 of the closure device 104 enclose the frame 110, but the closure device 104 does not also include the adhesive 128 or the removable divider 144 containing the primer 156. In such an embodiment, following the exit, and the expansion, of the closure device 104 from the distal end 404 of the sheath 400, as illustrated in FIG. 11B, the physician contacts the patient's tissues proximate the cardiac opening with the patch 124 of the closure device 104 and thermally welds the patch 124 to the patient's tissues. More specifically, in one embodiment, the physician generates a radio frequency current through the frame 110 enclosed within the hollow channels 136 of the patch 124. The resultant radio frequency energy applied to the patient's tissues proximate the cardiac opening, and to the patch 124 itself, heats the patient's tissues and the biological material from which the patch 124 is made. By applying this heat, and by also pressing the patch 124 against the patient's tissues proximate the cardiac opening, the physician fuses the patch 124 to the patient's tissues. Accordingly, the patch 124 of the closure device 104 is positioned across the cardiac opening to substantially occlude the cardiac opening. In one embodiment, the physician then retracts the frame 110 from within the patch 124 and removes the frame 110, along with the sheath 400 and the delivery catheter 108, from the patient's body.

Figure 11E:
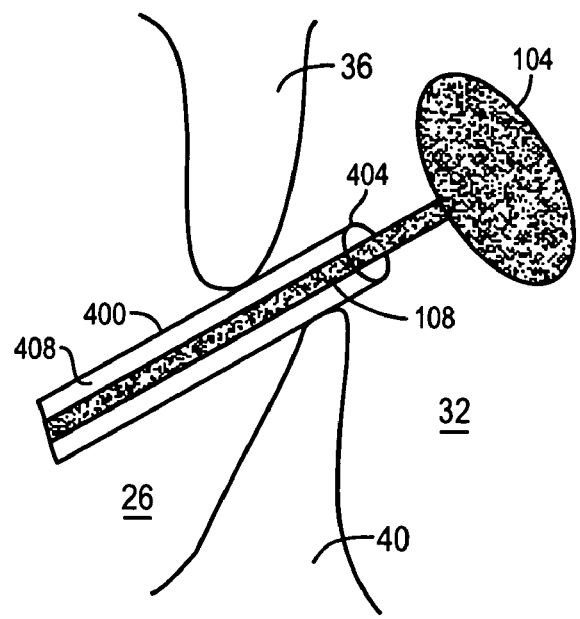
FIG. 11E-11F illustrates the stages, according to another illustrative embodiment of the invention, for closing a patent foramen ovale in a patient.
Figure 11F:
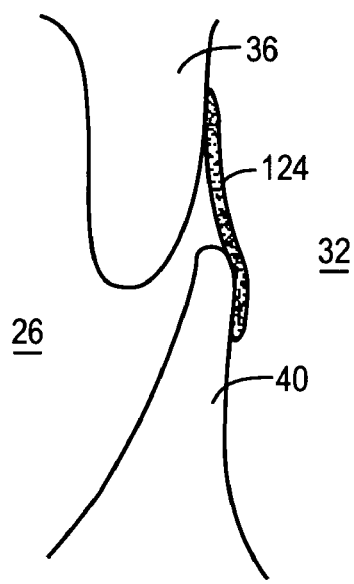

In accordance with the methods described above, where the cardiac opening under repair is a patent foramen ovale, the closure device 104 may be deployed in the right atrium 26, as illustrated in FIG. 11B, and the patch 124 may be bonded to the right atrial walls of the septum primum 40 and the septum secundum 36, as illustrated in FIG. 11C. Alternatively, in another embodiment in accordance with the methods described above, the sheath 400 is advanced through the patent foramen ovale and the closure device 104 is deployed in the left atrium 32, as illustrated in FIG. 11E. In such an embodiment, by proximally withdrawing the closure device 104 to contact the left atrial walls of the septum primum 40 and the septum secundum 36, the patch 124 may be bonded thereto, as illustrated in FIG. 11F, in any of the manners described above.

Alternatively, in yet another embodiment, to substantially occlude a cardiac opening or to obliterate a left atrial appendage, the physician places the patch 124 within the cardiac opening or the left atrial appendage, and bonds it thereto.

To percutaneously close a patent foramen ovale using the closure device 304 of the invention, the physician first performs essentially the same steps as illustrated and described above with respect to FIGS. 11A and 11B. More specifically, in one embodiment, the physician positions the distal end 404 of the sheath 400 proximate the patent foramen ovale and advances the closure device 304, by means of a delivery catheter attached to the closure device 304, into and through the lumen 408 of the sheath 400 until the closure device 304 exits the distal end 404 of the sheath 400 and expands to a position proximate the patent foramen ovale.

Figure 12:
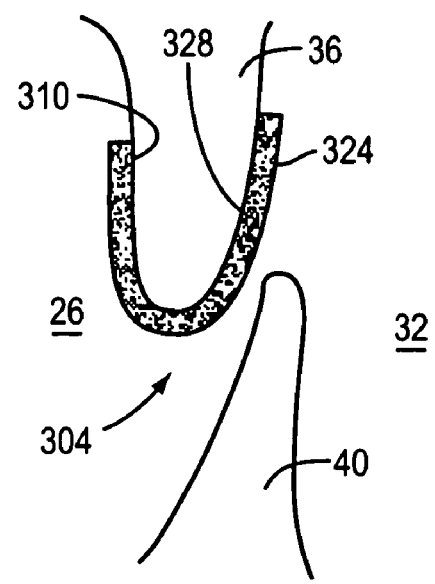
FIG. 12 is a schematic side view of the illustrative closure device of FIG. 7 coupled to the septum secundum of a patent foramen ovale.

Because the septum secundum 36 is rather thick in comparison to the septum primum 40, the physician then couples the inner surface 310 of the closure device 304, which contains the adhesive 328, to the septum secundum 36. Once the adhesive 328 has cured and glued to the septum secundum 36, the physician removes the delivery catheter from about the U-shaped patch 324 of the closure device 304, leaving the closure device 304 attached to the patient's septum secundum 36, as illustrated in FIG. 12.

As described above, the U-shaped patch 324 may include a substance that stimulates in-growth of the patient's tissue into the closure device 304 from either the septum secundum 36, the septum primum 40, or both the septum secundum 36 and the septum primum 40. Following placement of the closure device 304 on the septum secundum 36, as illustrated in FIG. 12, this tissue in-growth may be relied upon to substantially occlude the patent foramen ovale. Alternatively, as illustrated in FIGS. 8, 9, and 10, the closure device 304 may be further provided with either a right atrial barrier 314A, a left atrial barrier 314B, or both the right atrial barrier 314A and the left atrial barrier 314B to assist in closing the patent foramen ovale. The barriers 314A, 314B may include adhesives and may be bonded to the septum primum 40, as shown. Moreover, the barriers 314A, 314B may include substances that stimulate tissue in-growth into the closure device 304 from either the septum secundum 36, the septum primum 40, or both the septum secundum 36 and the septum primum 40.

In yet another aspect, the invention provides a compound for percutaneous transluminal closure of a cardiac opening, such as a patent foramen ovale, or for percutaneous transluminal obliteration of a cardiac cul-de-sac, such as a left atrial appendage. In one embodiment, the compound is used alone to close the cardiac opening or to obliterate the cardiac cul-de-sac. In another embodiment, the compound is used together with a closure device 104, 204, or 304.

Figure 13:
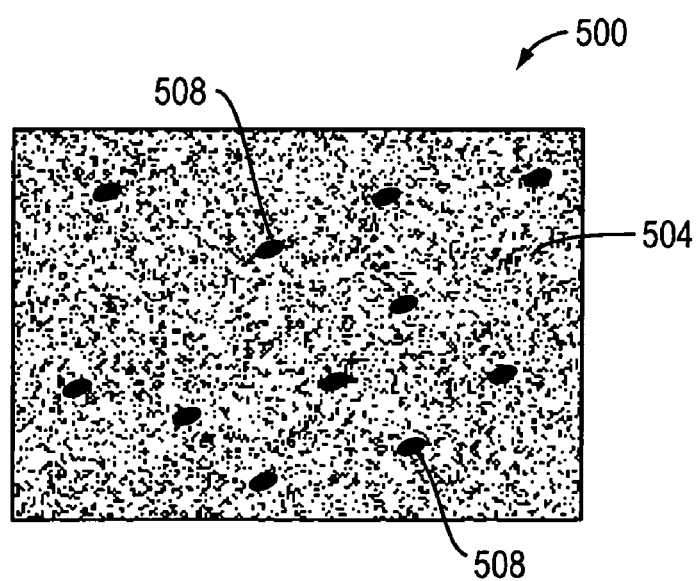
FIG. 13 illustrates a compound for the percutaneous transluminal closure of a cardiac opening according to an illustrative embodiment of the invention.

FIG. 13 depicts an exemplary compound 500 in accordance with this aspect of the invention. As illustrated, the compound 500 includes an adhesive 504 and a plurality of composite particles 508 disposed within the adhesive 504. In one embodiment, the plurality of composite particles 508 are capable of expansion upon contact with blood and/or water. The composite particles 508 are, for example, gelatin particles, biological particles, bioresorbable particles, and/or foam particles that swell upon contact with blood and/or water. In one embodiment, the adhesive 504 is a fibrin based adhesive. Alternatively, in other embodiments, the compound 500 includes other types of adhesives 504. Moreover, the adhesive 504 may be a permanent adhesive in the sense that, following placement of the adhesive 504 into the cardiac opening, the adhesive 504 permanently remains in the cardiac opening over time. Alternatively, in another embodiment, the adhesive 504 is a temporary adhesive that gradually disappears over time after having been placed in the cardiac opening. Mixed into the adhesive 504 may be a substance that promotes tissue in-growth into the cardiac opening over time.

In one embodiment, a physician positions the distal end of the sheath proximate the cardiac opening. The physician then advances, for example, a delivery catheter containing the compound 500 through a lumen of the sheath, until the delivery catheter exits the distal end of the sheath to lie within the cardiac opening. The physician then injects the compound 500 into the cardiac opening. Once injected into the cardiac opening and upon contact with the surrounding blood and/or water, the plurality of composite particles 508 disposed within the adhesive 504 of the compound 500 expand. By expanding, the plurality of composite particles 508 help to lock the adhesive 504 into place and to prevent the adhesive 504 from being washed away by the surrounding blood. More specifically, upon being injected into the cardiac opening, the adhesive 504 of the compound 500 cures both to the patient's surrounding tissue and to the plurality of expanding composite particles 508. As a result, the compound 500 substantially occludes the cardiac opening such as a patent foramen ovale. Similar steps may be performed to substantially obliterate an intra-cardiac cul-de-sac, such as the left atrial appendage.

In addition to closing the cardiac opening or obliterating the cardiac cul-de-sac on its own, the compound 500 may also be used in conjunction with the closure devices 104, 204, and 304 described above. For instance, after the compound 500 is injected into a patent foramen ovale or a left atrial appendage, or as the compound 500 is being injected, the patch 124 of the closure device 104 or the releasable patch 224 of the closure device 204 may be positioned across the cardiac opening, for example the patent foramen ovale or across the intra-cardiac cul-de-sac such as the left atrial appendage and coupled to the proximate tissue surface. Alternatively, prior to injecting the compound 500 into a patent foramen ovale, the closure device 304, including either or both the right atrial barrier 314A and the left atrial barrier 314B, described above, may be bonded to the septum secundum 36, as described above. The above-described patch 124 of the closure device 104, the releasable patch 224 of the closure device 204, and/or the atrial barriers 314A, 314B of the closure device 304 can thus be used to ensure that the adhesive 504 of the compound 500 remains in the cardiac opening and can also be used to aid the compound 500 in occluding the cardiac opening or the cardiac cul-de-sac, or in obliterating the cardiac cul-de-sac.

Figure 14:
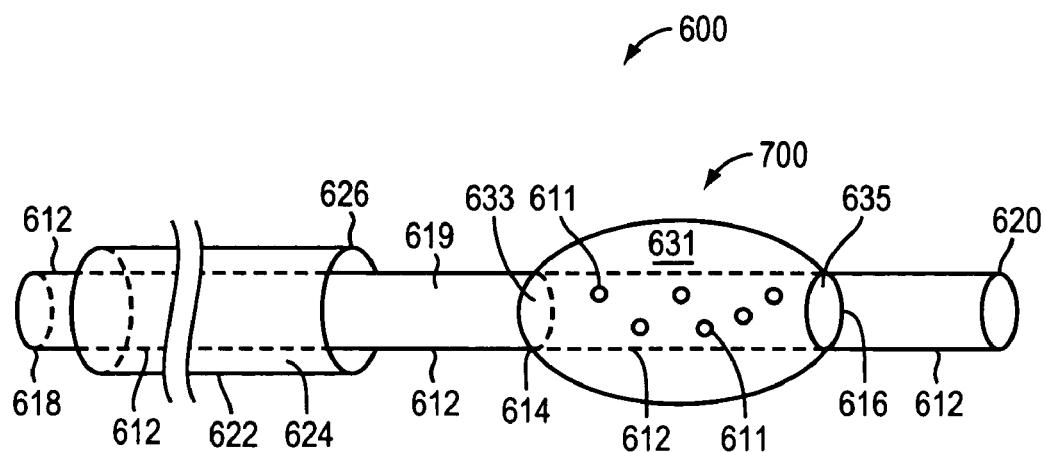
FIG. 14 is a schematic side view of a closure system according to an illustrative embodiment of the invention.

Referring now to embodiments of closure devices that include a balloon, FIG. 14 depicts an exemplary percutaneous transluminal system 600 for positioning a balloon 700 in, for example, the patent foramen ovale 44 or the left atrial appendage 80 described above. In one embodiment the closure system 600 includes the balloon 700 coupled to a balloon catheter 612. In accordance with the invention, either an adhesive, a substance for stimulating tissue growth, or both an adhesive and a substance for stimulating tissue growth is coated on, or contained within, the balloon 700. In use, the balloon 700 may be placed within a cardiac opening, such as a patent foramen ovale of the patient. Once placed within the cardiac opening, the balloon 700 may be manipulated to deliver the adhesive and/or the substance for stimulating tissue growth to the tissue surface of the cardiac opening. In one embodiment, the balloon 700 is then released from the balloon catheter 612 and left behind in the cardiac opening, while the balloon catheter 612 is removed from the patient. In such a case, the balloon 700 assists in closing the cardiac opening. Similar steps may be performed to close a cardiac cul-de-sec. Alternatively, in another embodiment, the balloon 700 is, after having delivered the adhesive and/or the substance for stimulating tissue growth to the tissue surface of a cardiac opening, removed from the cardiac opening and withdrawn from the patient along with the balloon catheter 612. In this case, the cardiac opening is encouraged to heal itself.

Figure 15:
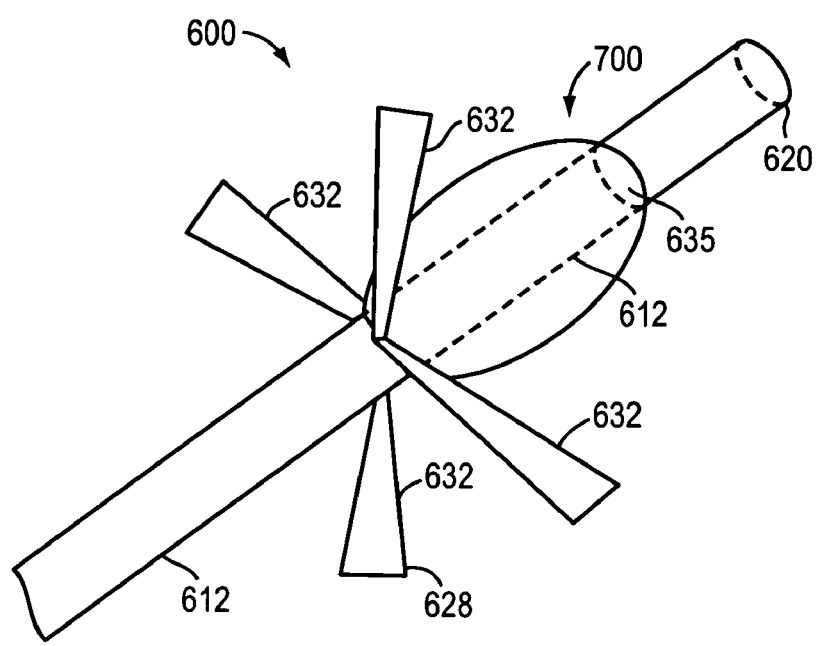
FIG. 15 is a schematic perspective view of a closure system according to another illustrative embodiment of the invention.
Figure 16:
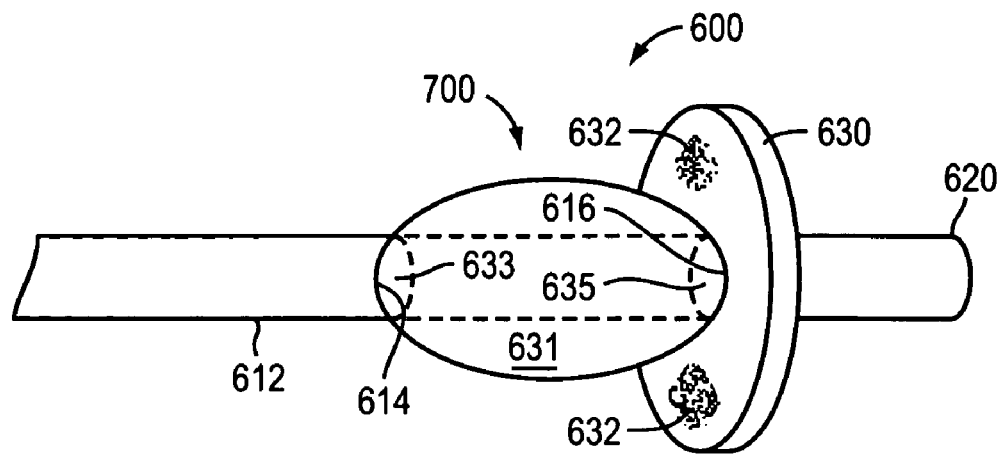
FIG. 16 is a schematic side view of a closure system according to another illustrative embodiment of the invention.
Figure 17:
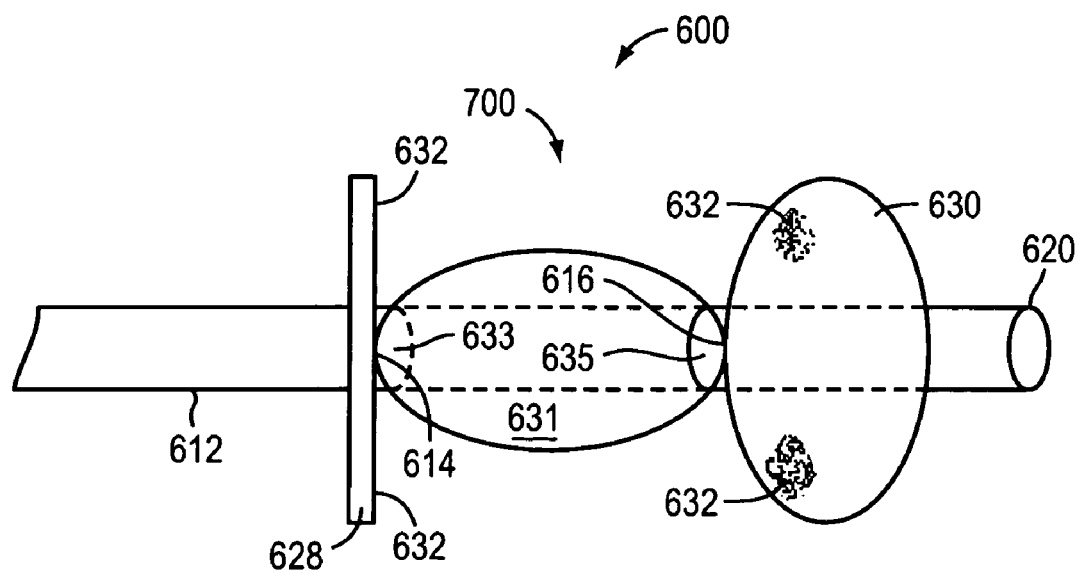
FIG. 17 is a schematic side view of a closure system according to another illustrative embodiment of the invention.

Referring briefly to FIGS. 15-17, to help locate a cardiac opening and properly position the balloon 700 within the cardiac opening, the closure system 600 includes, in some embodiments, a proximal locator 628 (i.e., a locator that is closest to a physician when the physician is using the closure system 600), an opposite, distal locator 630, or both the proximal locator 628 and the distal locator 630. In use, the locator 628 locates a proximal end of a cardiac opening. The locator 630 locates a distal end of the cardiac opening.

Referring again to FIG. 14, the balloon 700 includes a proximal end 614 and an opposite, distal end 616. In one embodiment, the balloon 700 also includes a proximal opening 633 at its proximal end 614, a distal opening 635 at its distal end 616, and a lumen 631 extending from its proximal end 614 to its distal end 616. For its part, the balloon catheter 612 includes a proximal end 618, an opposite, distal end 620, and a lumen 619 extending from the proximal end 618 to the distal end 620. In the illustrative embodiment shown, the balloon catheter 612 extends through the proximal opening 633, through the lumen 631, and through the distal opening 635 of the balloon 700 so that the entire balloon 700 is located between the proximal end 618 and the distal end 620 of the balloon catheter 612. In such an embodiment, the portion of balloon catheter 612 located within the balloon 700 includes a plurality of holes 611. Accordingly, the lumen 619 of the balloon catheter 612 is in fluid communication with the lumen 631 of the balloon 700. In another embodiment, the distal end 620 of the balloon catheter 612 is coupled to the proximal end 614 of the balloon 700 such that the lumen 619 of the balloon catheter 612 is contiguous with the lumen 631 of the balloon 700. Alternatively, in yet another embodiment, the distal end 620 of the balloon catheter 612 extends through the proximal opening 633 and is located within the lumen 631 of the balloon 700.

In one embodiment, the balloon 700 is releasably coupled to the balloon catheter 612. For example, the balloon 700 is coupled to the balloon catheter 612 so that it may be separated from the balloon catheter 612 by applying a force, such as compression, tension, torsion, or any other type of force. In this embodiment, the balloon 700 is left within the cardiac opening to assist in closing the cardiac opening. In another embodiment, the balloon 700 is permanently coupled to the balloon catheter 612 for removal from the patient's body along with balloon catheter 612.

FIG. 14 also depicts a delivery catheter 622 having a lumen 624. In one embodiment, to deliver the balloon 700 to a cardiac opening in a patient, the physician first places a distal end 626 of the delivery catheter 622 in the patient's heart proximate the cardiac opening. The physician then places the closure system 600 in the lumen 624 of the delivery catheter 622 and advances the closure system 600 through the lumen 624 of the delivery catheter 622 until the closure system 600 exits the distal end 626 of the delivery catheter 622, as shown. Methods of delivering the balloon 700 to the patient are described further below.

FIGS. 15-17 depict the percutaneous transluminal closure system 600 for positioning the balloon 700 in a cardiac opening of a patient according to alternative illustrative embodiments of the invention. As depicted in FIG. 15, the closure system 600 includes, in one embodiment, an expandable proximal locator 628 for locating a proximal end of a cardiac opening. The locator 628 may be, as shown, coupled to the balloon catheter 612, to the proximal end 614 of the balloon 700, or to both the balloon catheter 612 and the balloon 700. In one embodiment, the locator 628 is a right atrial locator for locating a patent foramen ovale 44 from the right atrium 26. When expanded, the locator 628 is configured to abut the tissue surfaces of the septum secundum 36 and the septum primum 30 from the right atrium 26 as the balloon 700 is placed within the patent foramen ovale 44. Accordingly, the locator 628 locates the patent foramen ovale 44. In another embodiment, the locator 628 is used for locating an exterior tissue surface of a left atrial appendage 80. In this case, the locator 628 is configured to abut the exterior tissue surface of the left atrial appendage 80 as the balloon 700 is placed within the left atrial appendage 80.

In another embodiment, as depicted in FIG. 16, the closure system 600 includes an expandable distal locator 630 for locating a distal end of a cardiac opening. More specifically, the locator 630 is a left atrial locator for locating a patent foramen ovale 44 from the left atrium 32. The locator 630 may be, as shown, coupled to the balloon catheter 612, to the distal end 616 of the balloon 700, or to both the balloon catheter 612 and the balloon 700. In use, a physician advances the balloon 700 from the right atrium 26, through the patent foramen ovale 44, to the left atrium 32. The physician then expands the locator 630 in the left atrium 32 and withdraws the balloon 700 from the left atrium 32 back into the patent foramen ovale 44. The locator 630 is configured to abut the tissue surfaces of the septum secundum 36 and the septum primum 40 from the left atrium 32 as the balloon 700 is placed within the patent foramen ovale 44. Accordingly, the locator 630 locates the patent foramen ovale 44 and properly positions the balloon 700 within the patent foramen ovale 44.

In yet another embodiment, and with reference now to FIG. 17, the closure system 600 includes two locators, a proximal locator 628 and a distal locator 630.

The locators 628, 630 may be made to expand by any of a variety of means. For example, in one embodiment, the locators 628, 630 include a plurality of springs or resilient coils that cause them to expand. In another embodiment, the locators 628, 630 are balloons that are inflated. The locators 628, 630 may be made from an elastomer material, such as a polyurethane or a silicone, from a biological material, such as a collagen or a bioresorbable polymer, or from other materials, such as synthetic materials. In yet another embodiment, the locators 628, 630 are made from a metallic material or a shape memory material, such as a shape memory alloy.

A plurality of arms, as illustrated for the proximal locator 628 in FIG. 15, may form the locators 628, 630. Alternatively, the locators 628, 630 may each be shaped as a disk, as illustrated for the distal locator 630 in FIG. 16, as a balloon, as illustrated for the distal locator 630 in FIG. 17, or as a rod, as illustrated for the proximal locator 628 in FIG. 17. Any other geometry deemed suitable by one skilled in the art, such as, for example, a spiral wire, may also be used for the locators 628, 630. In one embodiment, the locators 628, 630 are releasably coupled to the balloon 700 and/or to the balloon catheter 612. For example, the locators 628, 630 are coupled to the balloon 700 and/or to the balloon catheter 612 so that they may be separated from the balloon 700 and/or the balloon catheter 612 by applying a force, such as compression, tension, torsion, or any other type of force. In another embodiment, the locators 628, 630 are permanently coupled to the balloon 700 and/or to the balloon catheter 612 for removal from the patient's body along with the balloon 700 and/or the balloon catheter 612.

In another embodiment, an adhesive 632 is coated on the locators 628, 630. The adhesive 632 may be used, for example, to bond the locators 628, 630 to the wall of the septum secundum 36 and/or to the wall of the septum primum 40 when the balloon 700 is used to close a patent foramen ovale 44. Alternatively, the adhesive 632 may be used to bond the proximal locator 628 to a tissue surface proximate a left atrial appendage 80 when the balloon 700 is used to obliterate the left atrial appendage 80. The adhesive 632 may be, for example, a cyanoacrylate, a fibrin based adhesive, or an albumin gluteraldehyde type adhesive.

Figure 18:
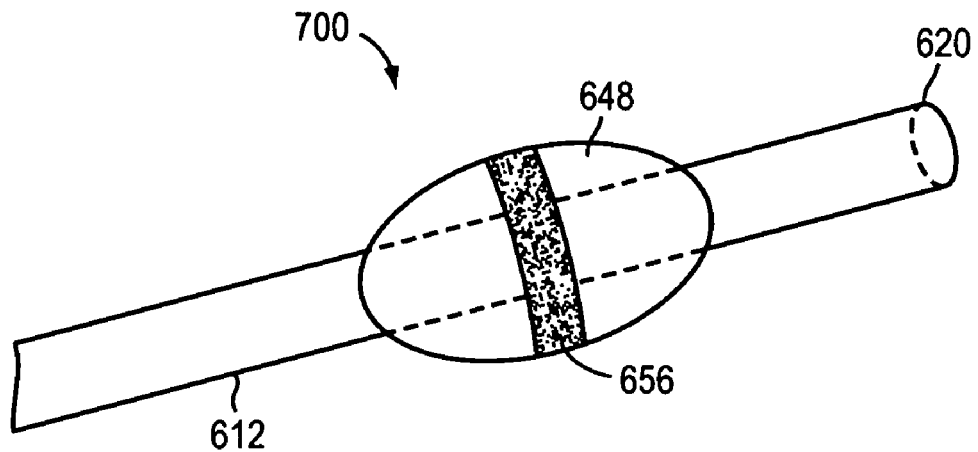
FIG. 18 is a schematic perspective view of an inflated balloon according to an illustrative embodiment of the invention.
Figure 19:
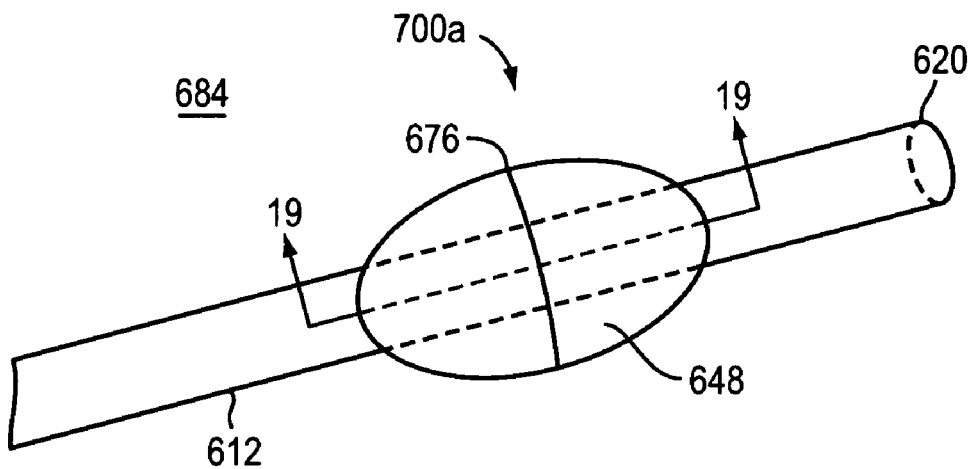
FIG. 19 is a schematic perspective view of the illustrative balloon of FIG. 17 deflated according to an illustrative embodiment of the invention.
Figure 20:
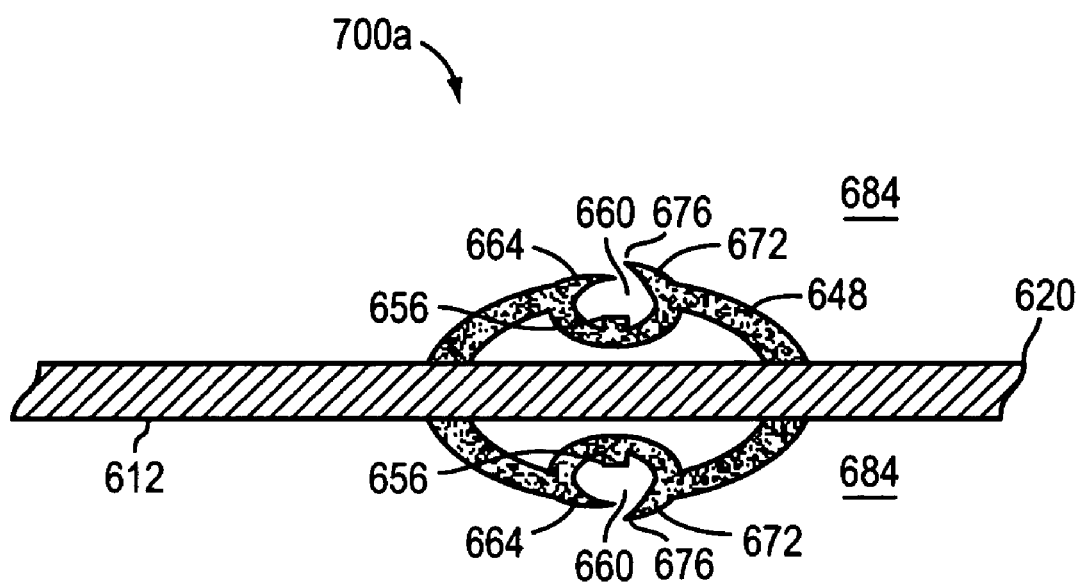
FIG. 20 is a schematic cross-sectional view of the illustrative balloon of FIG. 19 taken along the line 19-19.

FIG. 18 depicts an inflated balloon, generally 700, having an outer surface 648. In one embodiment, an adhesive 656 is coated on the outer surface 648 of the balloon $700^a$. FIG. 19 depicts the balloon $700^a$ deflated or partially deflated and FIG. 20 depicts a schematic cross-sectional view of the balloon $700^a$ of FIG. 19 taken along the line 19-19. Typically, the balloon $700^a$ of the invention is coupled to the balloon catheter 612, as described previously, and is initially delivered to a cardiac opening in a heart of a patient with the balloon $700^a$ deflated or partially deflated.

Referring to FIG. 20, the outer surface 648 of the deflated or partially deflated balloon $700^a$ is involuted to form a cavity 660 around the circumference of the outer surface 648 of the balloon $700^a$. In one embodiment, the midline 676 of the outer surface 648 of the balloon $700^a$ is pushed towards the inside of the balloon $700^a$ to form the cavity 660. The edges 664, 672 of the cavity 660 are folded to contact or overlap one another, as illustrated. By folding the balloon $700^a$ as such, the outer surface 648 of the balloon $700^a$ seals the cavity 660 from exposure to an outside environment 684.

Figure 21:
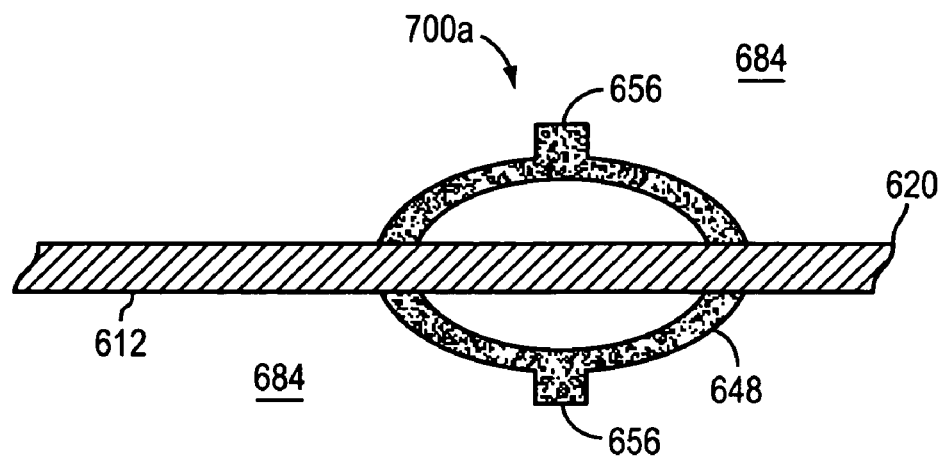
FIG. 21 is a schematic cross-sectional view of the illustrative balloon of FIG. 20 inflated according to an illustrative embodiment of the invention.
Figure 22:
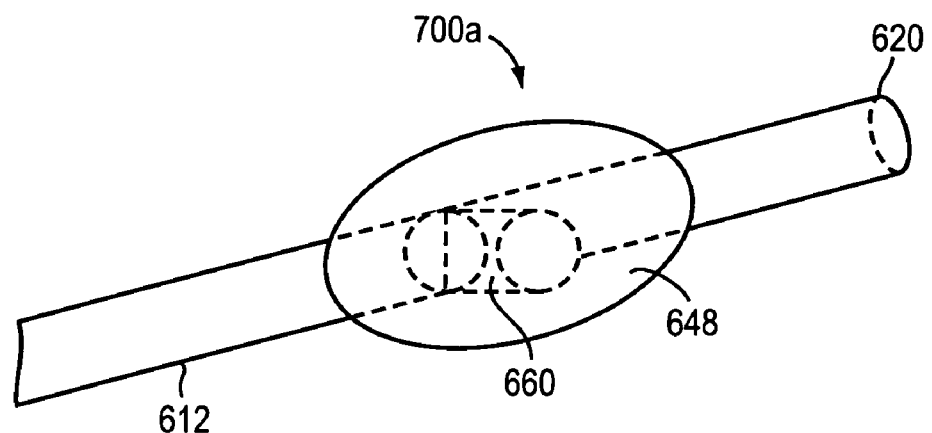
FIG. 22 is a schematic perspective view of a deflated balloon according to another illustrative embodiment of the invention.

In one embodiment, adhesive 656 is coated on the surface of the cavity 660 of the deflated or partially deflated balloon $700^a$. Accordingly, when the balloon $700^a$ is deflated or partially deflated, the adhesive 656 is also sealed from exposure to the outside environment 684. By delivering the balloon $700^a$ to the patient's cardiac opening with the balloon $700^a$ deflated, the adhesive 656 is not exposed to the patient's blood and, according to one advantage of the invention, the risk of thrombus formation is thereby minimized. Once properly positioned within a patient's cardiac opening, the balloon $700^a$ may be inflated, thereby causing the involuted cavity 660 to unfold, as illustrated in FIG. 21, and exposing the adhesive 656 to the patient's tissues within the cardiac opening. Although the cavity 660 has been shown encircling the mid-portion of the balloon $700^a$, the cavity 660 may encircle in any orientation any portion of the outer surface 648 of the balloon $700^a$ and in fact may be restricted to being simply an involuted pocket in a portion of the outer surface 648 of the balloon $700^a$, as illustrated in FIG. 22.

Figure 23:
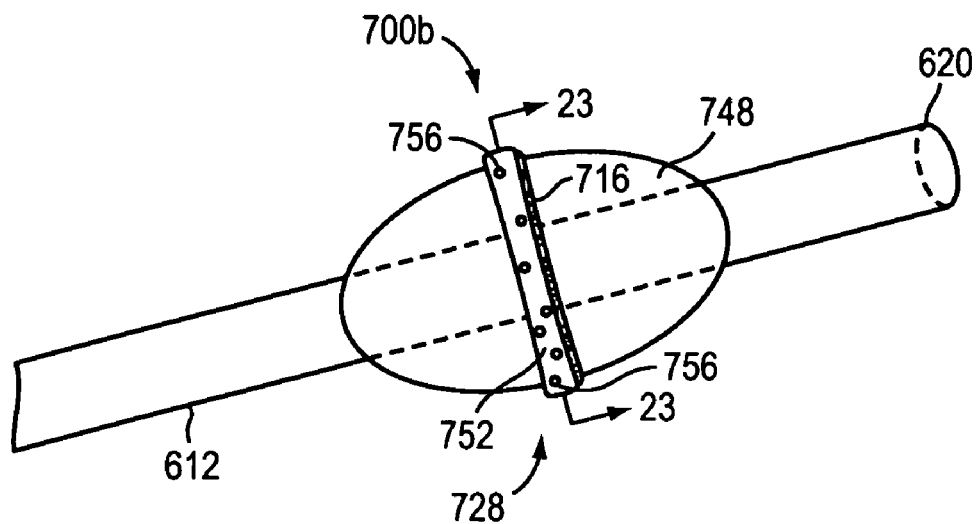
FIG. 23 is a schematic perspective view of a balloon according to another illustrative embodiment of the invention.

FIG. 23 depicts an embodiment of a balloon $700^b$. The balloon $700^b$ has an outer surface 748. An expandable porous band 752 (e.g., an elastic band 752), having a plurality of openings 756, encircles, in one embodiment, only a portion of the outer surface 748 of the balloon $700^b$, such as the center portion 728 of the balloon $700^b$. In alternative embodiments, the expandable porous band 752 encircles other portions of the balloon $700^b$. In one embodiment, an adhesive 716 is disposed between the outer surface 748 of the balloon $700^b$ and the expandable porous band 752. The expandable porous band 752 is designed such that, until the balloon $700^b$ is sufficiently inflated, the openings 756 of the porous band 752 are too small to allow any of the adhesive 716 to pass therethrough. By ensuring that the balloon $700^b$ is not sufficiently inflated, a physician can prevent the adhesive 716 from being inadvertently exposed to a patient's blood and can thereby avoid thrombus formation.

Figure 24:
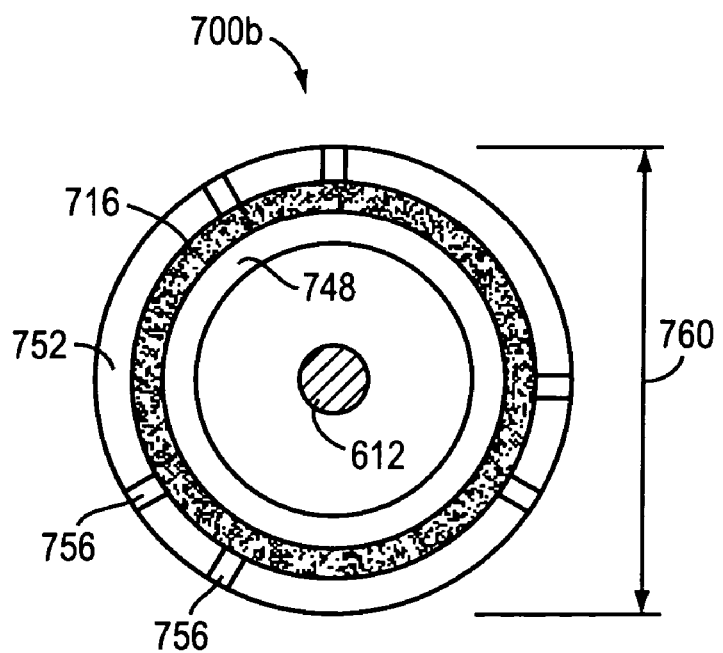
FIG. 24 is a schematic cross-sectional view of the illustrative balloon of FIG. 23 taken along the line 23-23.

FIG. 24 depicts a schematic cross-sectional view of the balloon $700^b$ of FIG. 23 taken along the line 23-23. When nearly sufficiently inflated, a cross-sectional diameter 760 of the center portion 728 of the balloon $700^b$ is, in one embodiment, slightly less than the inner circumference of the cardiac opening or the cardiac cul-de-sac that the balloon 700$^b$ is to close. For example, where the balloon 700$^b$ is used to close a patent foramen ovale 44, the center portion 728 of the balloon 700$^b$ is designed to have, when nearly sufficiently inflated, a cross-sectional diameter 760 between approximately 1 millimeter and approximately 25 millimeters. Alternatively, when the balloon 700$^b$ is used to close a left atrial appendage 80, the center portion 728 of the balloon 700$^b$ is designed to have, when nearly sufficiently inflated, a cross-sectional diameter 760 between approximately 5 millimeters and approximately 25 millimeters.

Figure 25:
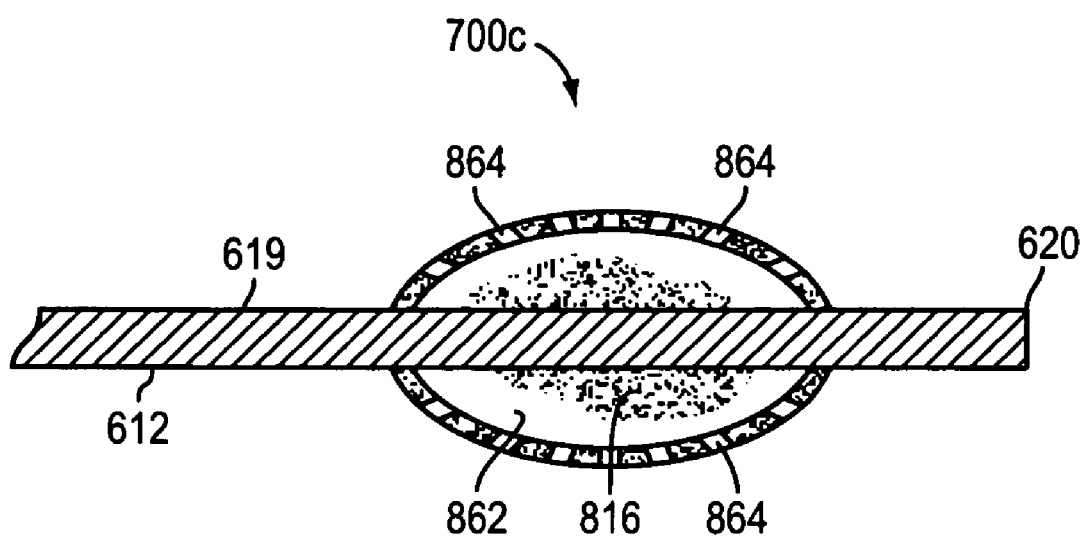
FIG. 25 is a schematic cross-sectional view of a balloon according to another illustrative embodiment of the invention.

FIG. 25 depicts another embodiment of a balloon 700$^c$. Contained within the lumen 862 of the balloon 700$^c$ is an adhesive 816. The balloon 700$^c$ has a plurality of holes 864. In various embodiments, the holes 864 are pores or slits. Until sufficiently inflated, the balloon 700$^c$ will not have expanded and/or stretched to a point where the holes 864 are large enough to allow the adhesive 816 to pass therethrough.

Figure 26:
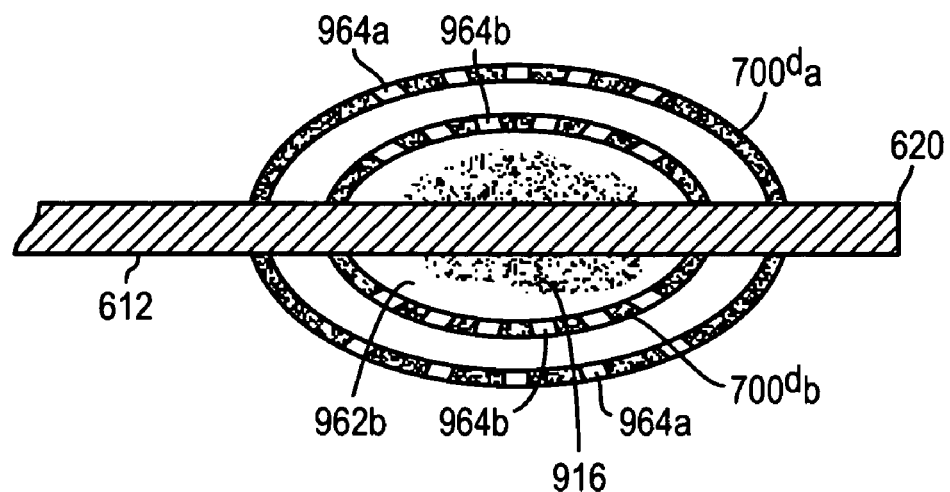
FIG. 26 is a schematic cross-sectional view of concentric balloons according to another illustrative embodiment of the invention.

FIG. 26 depicts yet another illustrative embodiment of the invention. This embodiment includes two concentric balloons 700$^d$A, 700$^d$B and an adhesive 916 located within the lumen 962B of the inner balloon 700$^d$B. In one embodiment, the outer balloon 700$^d$A and the inner balloon 700$^d$B each include a plurality of holes (e.g., pores or slits) 964A and 964B, respectively.

Once the balloon 700$^{b,\ c,\ or\ d}$ is placed within the cardiac opening or the cardiac cul-de-sac of a patient and is nearly sufficiently inflated, the further application of pressure to the balloon 700$^{b,\ c,\ or\ d}$ enlarges the openings 756 of the porous band 752, the holes 864, or the holes 964, respectively. The adhesive is thereby forced through the openings 756, the holes 864, or the holes 964 to the tissue surface of the cardiac opening or the cardiac cul-de-sac. A physician may apply the further pressure to the balloon 700$^{b,\ c,\ or\ d}$ by further inflating the lumen of the balloon 700$^{b,\ c,\ or\ d}$. For example, to further inflate the lumen 862 of the balloon 700$^c$, the physician pumps additional adhesive 816 through the lumen 619 of the balloon catheter 612 into the lumen 862 of the balloon 700$^c$. Alternatively, compression of a part of the balloon 700$^{b,\ c,\ or\ d}$ by, for example, contacting the tissue surface of the cardiac opening or the cardiac cul-de-sac with that part of the balloon 700$^{b,\ c,\ or\ d}$, thus further inflating the remaining portions of the balloon 700$^{b,\ c,\ or\ d}$, will also cause the adhesive to be exposed to the tissue surface. In certain embodiments, the adhesive is only exposed to the patient's tissues in the area where the balloon 700$^{b,\ c,\ or\ d}$ contacts the patient's tissues. For example, in one embodiment, the adhesive is only exposed in the area where the patient's tissues compress the balloon 700$^{b,\ c,\ or\ d}$.

Figure 27:
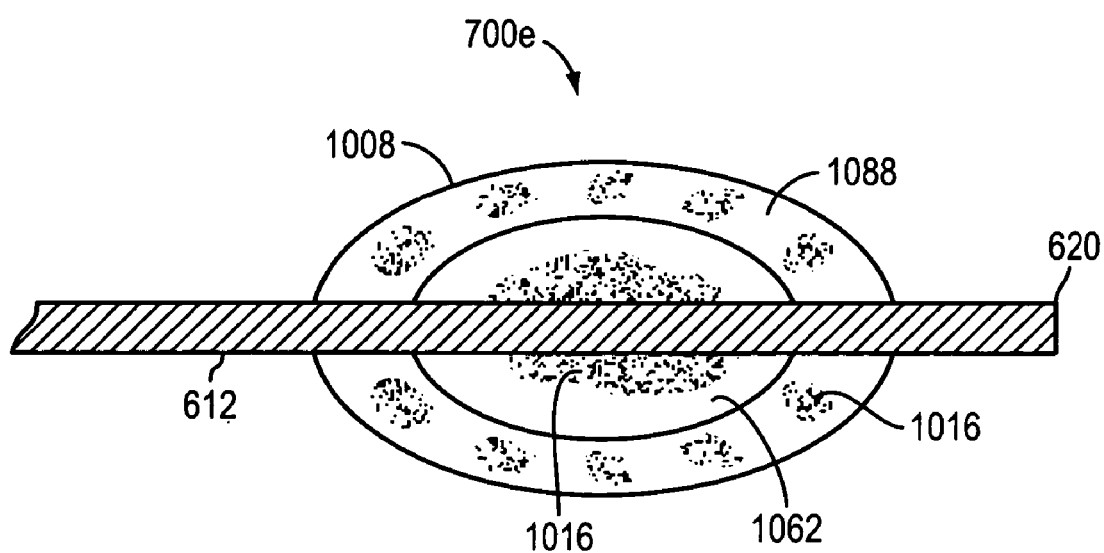
FIG. 27 is a schematic cross-sectional view of a balloon according to another illustrative embodiment of the invention.

FIG. 27 depicts a balloon 700$^e$ having a membrane 1088 constructed from a wicking material. The wicking material may be, for example, a natural fiber, such as cotton. In one embodiment, an adhesive 1016 is absorbed within the wicking material of the balloon membrane 1088. The adhesive 1016 is naturally drawn, by capillary action, to the outer surface 1008 of the balloon 700$^e$. Additionally, as shown, the adhesive 1016 may also be contained within a lumen 1062 of the balloon 700$^e$.

Once the balloon 700$^e$ is placed within, for example, the cardiac opening, contacting the tissue surface of the cardiac opening with the membrane 1088 of the balloon 700$^e$ draws, by capillary action, further adhesive 1016 absorbed within the membrane 1088 to the outer surface 1008 of the balloon 700$^e$. The tissue surface of the cardiac opening is thereby coated with the adhesive 1016.

Figure 28:
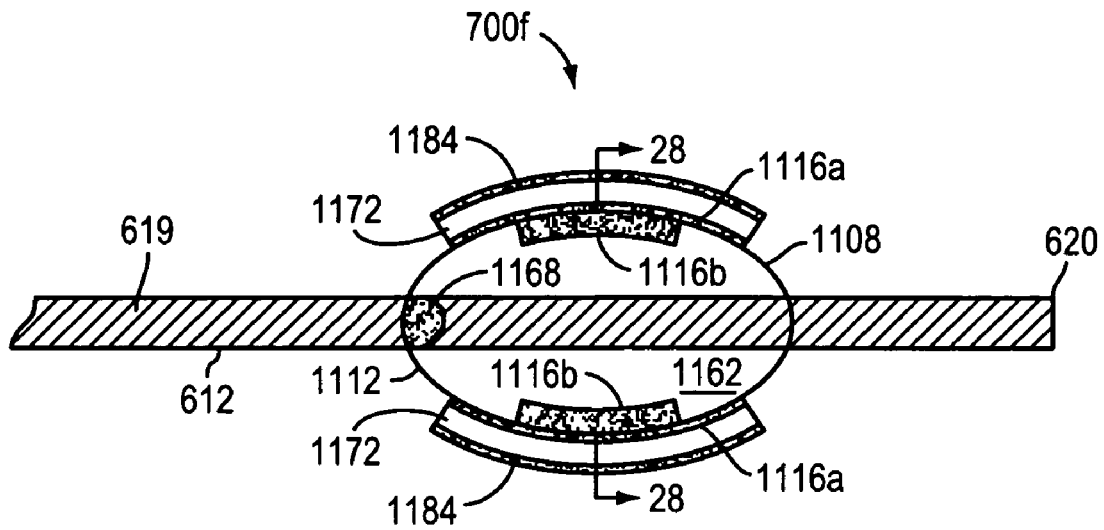
FIG. 28 is a schematic cross-sectional view of a balloon according to another illustrative embodiment of the invention.

FIG. 28 depicts still another embodiment of the invention. As shown, a balloon 700$^f$ has a first adhesive 1116A coated on an outer surface 1108 of the balloon 700$^f$. A light source 1168 is located within the lumen 619 of the balloon catheter 612 and within a lumen 1162 of the balloon 700$^f$. The balloon catheter 612 may be translucent, or, alternatively, may includes holes in the region of the light source 1168, to allow the light emitted by the light source 1168 to propagate outside the balloon catheter 612. The light source 1168 is, in one embodiment, a light bulb coupled through the balloon catheter 612 to a power supply. In another embodiment, the light source 1168 is an optical fiber connected at its other end to a source of illumination.

In yet another embodiment, a second adhesive 1116B is coated on an inner surface 1112 of the balloon 700$^f$. The first adhesive 1116A and/or the second adhesive 1116B may each be, for example, a light activated adhesive, such as an adhesive curable with ultraviolet light. The first adhesive 1116A and the second adhesive 1116B may cover only a portion of the outer surface 1108 of the balloon 700$^f$ and the inner surface 1112 of the balloon 700$^f$, respectively, as shown, or they may cover the entire outer surface 1108 and inner surface 1112, respectively. In one embodiment, the balloon 700$^f$ is translucent.

Figure 29:
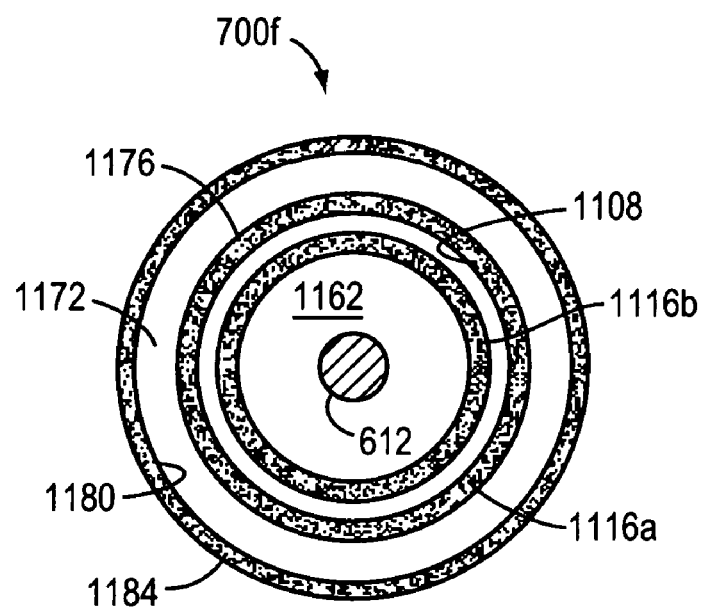
FIG. 29 is a schematic cross-sectional view of the illustrative balloon of FIG. 28 taken along the line 28-28.

FIG. 29 depicts a schematic cross-sectional view of the balloon 700$^f$ of FIG. 28, taken along the line 28-28. As shown in FIGS. 28 and 29, the balloon 700$^f$ further includes, in one embodiment, a first non-reactive removable divider 1172. The divider 1172 is coupled to the balloon 700$^f$ so that one surface 1176 of the divider 1172 contacts the first adhesive 1116A coated on the outer surface 1108 of the balloon 700$^f$. Coated on the second surface 1108 of the divider 1172 is a primer 1184. In one embodiment, the primer 1184 prepares the tissue surface of the patient to which the adhesive 116A will be applied. In another embodiment, the primer 1184 helps to activate the adhesive 1116A and/or bond the adhesive 1116A to the patient's tissue surface.

In another embodiment, a second removable divider or temporary membrane (not shown) covers the primer 1184 to protect it against premature exposure to blood. The second removable divider or temporary membrane may have attached to it sutures that can be pulled upon by the physician to remove it from the primer 1184 when the physician is ready to apply the primer 1184 to the tissues of the patient's cardiac opening. Similarly, in one embodiment, the first removable divider 1172 has attached to it sutures that can be pulled upon by the physician to remove it from the adhesive 1116A when the physician is ready to apply the adhesive 1116A to the tissues of the patient's cardiac opening.

The balloons 700 described above may be tubularly-shaped. In alternative embodiments, the balloons 700 have other shapes, such as, for example, circular or rectangular shapes. The adhesives coated on, or contained within, the balloons 700 of the invention may be, for example, cyanoacrylates, fibrin based adhesives, albumin gluteraldehyde type adhesives, or light activated adhesives. Alternatively, other adhesives, known to those skilled in the art, may be used.

In some embodiments, the balloons 700 include a substance for stimulating tissue growth. The growth substance may be combined with the adhesives of the balloons 700 or be used independently. In fact, the growth substance may be applied to, or be positioned within, the balloons 700 in the same manner as described above for the adhesives of the balloons 700. In one embodiment, the growth substance is, for example, a growth factor, such as a vascular endothelial growth factor, a basic fibro growth factor, or an angiogenic growth factor. In another embodiment, the growth substance is a pharmacological agent for stimulating tissue growth, such as, for example, cells or genes. Alternatively, in another embodiment, the growth substance is an irritant for encouraging an inflammatory response, such as, for example, cotton seed oil or alcohol.

The balloons 700$^{a, b, c, d, and f}$ described above are, in one embodiment, made from an elastomer material, such as, for example, a polyurethane or a silicone. In another embodiment, the balloons 700$^{a, b, c, d, and f}$ are made from a biological material, such as, for example, a collagen or a bioresorbable polymer. Alternatively, the balloons 700$^{a, b, c, d, and f}$ are made from other materials.

Figure 30:
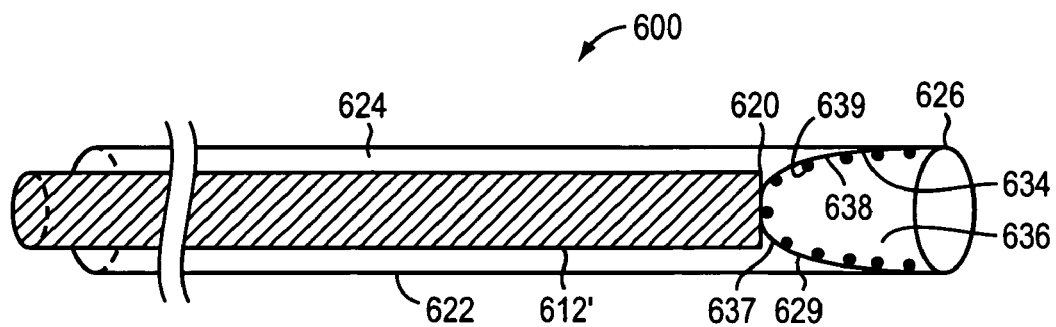
FIG. 30 is a schematic side view of a closure system, including a retracted sock catheter, according to another illustrative embodiment of the invention.
Figure 31:
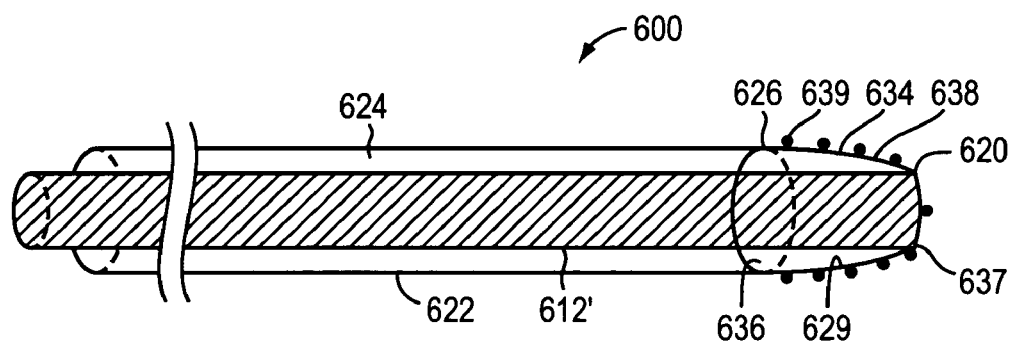
FIG. 31 is a schematic side view of the illustrative closure system of FIG. 30, including a deployed sock catheter.

FIG. 30 depicts a closure system 600 according to still another illustrative embodiment of the invention. As illustrated, the exemplary closure system 600 includes the delivery catheter 622 described above, a sock catheter 612', and a sock-shaped lining 634. For its part, the lining 634 has an open end 636, a closed end 637, a first surface 638, and a second surface 629. In one embodiment, the open end 636 of the lining 634 is coupled to the distal end 626 of the delivery catheter 622 and the closed end 637 of the lining 634 is coupled to the distal end 620 of the sock catheter 612'. When the sock catheter 612' is retracted, as depicted in FIG. 30, the lining 634 is contained within the lumen 624 of the delivery catheter 622, the first surface 638 forms an inner surface of the sock-shaped lining 634, and the second surface 629 forms an outer surface of the sock-shaped lining 634. When the sock catheter 612' is deployed, as illustrated in FIG. 31, the lining 634 inverts. Consequently, the first surface 638 now forms an outer surface of the sock-shaped lining 634 and the second surface 629 forms an inner surface of the sock-shaped lining 634.

In the illustrative embodiment shown in FIGS. 30 and 31, an adhesive 639, similar to any of the adhesives used for the balloons 700 described above, is coated on the first surface 638 of the lining 634. Typically, a physician advances the closure system 600 with the sock catheter 612' retracted, as illustrated in FIG. 30, and, once the closure system 600 is proximate a cardiac opening, the physician deploys the sock catheter 612' so that it exits the distal end 626 of the delivery catheter 622, as illustrated in FIG. 31. In one embodiment, the physician deploys the sock catheter 612' by advancing (e.g., pushing) it distally or by withdrawing (e.g., pulling) the delivery catheter 622 proximally. Alternatively, in another embodiment, the sock catheter 612' is itself a balloon that may be expanded to exit the distal end 626 of the delivery catheter 622. By deploying the sock catheter 612', the lining 634 inverts to expose the first surface 638 and the adhesive 639 coated thereon to the patient's tissues.

In another embodiment, the lining 634 includes a plurality of holes (not shown). In one such embodiment, the adhesive 639 is coated on the second surface 629 of the lining 634 and/or is contained (e.g., absorbed) within the lining 634 itself. By deploying the sock catheter 612' as shown in FIG. 21, the lining 634 inverts and stretches, thereby enlarging the plurality of holes. Accordingly, the adhesive 639 may pass through the plurality of holes to the first surface 638 of the lining 634 for application to the patient's tissues.

In yet another embodiment, a substance for stimulating tissue growth, as described above, is combined with the adhesive 639 or is used independently.

In another aspect, the invention features methods for delivering a balloon 700 to a cardiac opening or a cardiac cul-de-sac in a patient and also methods for percutaneously closing the cardiac opening or obliterating the cardiac cul-de-sac using the delivered balloon 700. FIGS. 32A-32D depict the steps of an illustrative method for delivering a balloon 700 of the invention to a cardiac opening in a patient. The cardiac opening illustrated in FIGS. 32A-32D is a patent foramen ovale 44. However, as described below, the methods of the invention may also be used to obliterate a left atrial appendage 80.

Figure 32A:
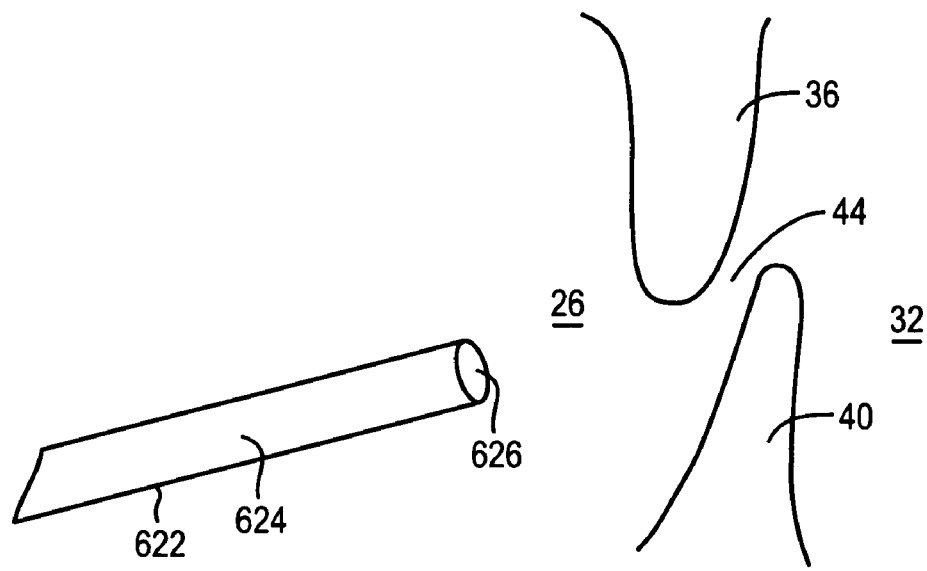
FIGS. 32A-32D illustrate the stages, according to an illustrative embodiment of the invention, for closing a patent foramen ovale in a patient.
Figure 32B:
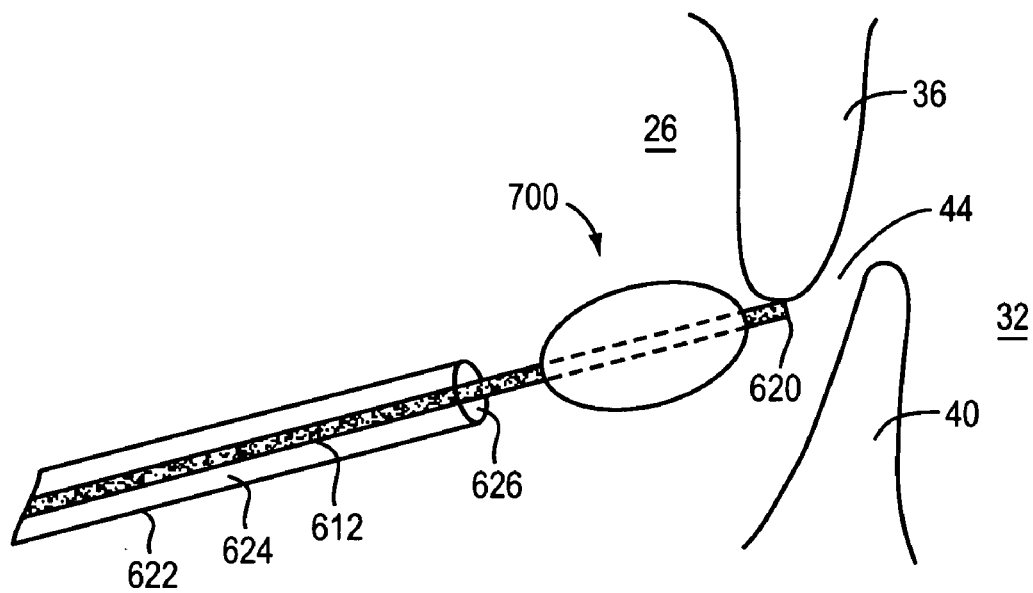

Referring to FIG. 32A, in one embodiment, a physician advances the delivery catheter 622 into the patient's heart and positions the distal end 626 of the delivery catheter 622 proximate the cardiac opening. The physician then advances the balloon 700 and the balloon catheter 612 into and through the lumen 624 of the delivery catheter 622. The physician continues to advance the balloon 700 until it and a distal portion of the balloon catheter 612 exit the distal end 626 of the delivery catheter 622 adjacent the cardiac opening, as illustrated in FIG. 32B. In one embodiment, a deflated balloon 700 exits the distal end 626 of the delivery catheter 622 and is kept deflated until appropriately positioned within the cardiac opening. The balloon 700 is then inflated. In another embodiment, the balloon 700 (e.g., the balloon 700$^f$ depicted in FIGS. 28 and 29) exits the distal end 626 of the delivery catheter 622 inflated, or, alternatively, exits deflated and is inflated by the physician prior to being positioned within the cardiac opening.

Figure 32C:
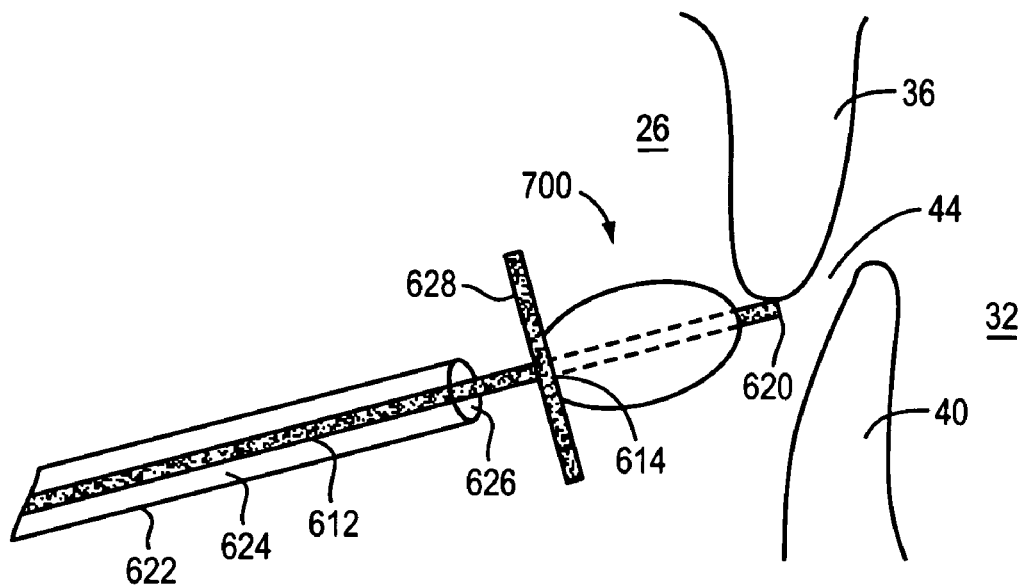
Figure 32D:
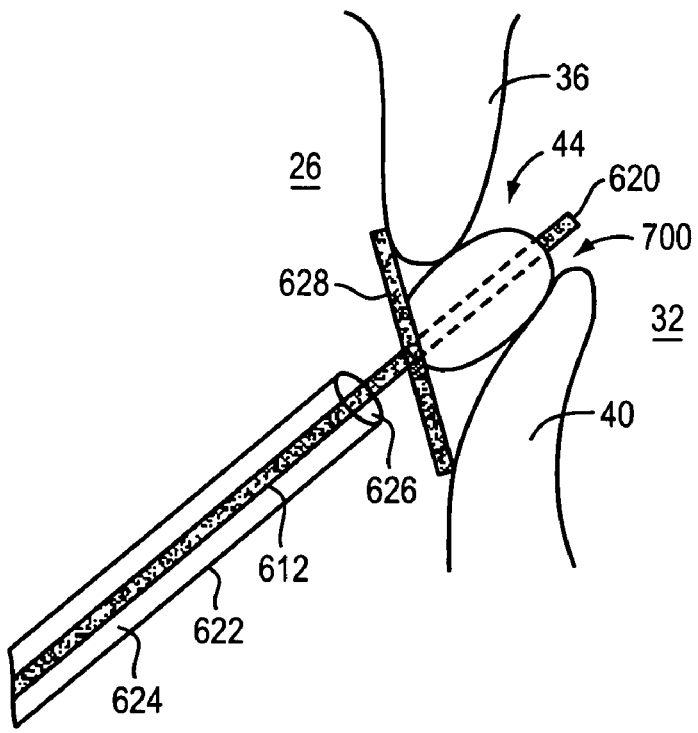

Referring now to FIG. 32C, after the balloon 700 exits the distal end 626 of the delivery catheter 622 and/or is inflated adjacent the cardiac opening by the physician, the physician, in one embodiment, expands the proximal locator 628 adjacent the cardiac opening. In one embodiment, with the locator 628 expanded as illustrated in FIG. 32C, the physician advances the balloon 700 into the cardiac opening. The physician continues to advance the balloon 700 into the cardiac opening until the locator 628 abuts a tissue surface proximate cardiac opening. For example, as depicted in FIG. 32D, the physician advances the balloon 700 into the patent foramen ovale 44 until the locator 628 abuts the proximal walls of the septum secundum 36 and the septum primum 40. Alternatively, where the left atrial appendage 80 is to be obliterated, the physician advances the balloon 700 into the left atrial appendage 80 until the locator 628 abuts the tissue surface of the heart proximate the left atrial appendage 80. Having used the locator 628 to locate the cardiac opening, the physician then uses the locator 628 to correctly position the balloon 700 within the cardiac opening. In one embodiment, the balloon 700 is correctly positioned within the cardiac opening when the locator 628 abuts the tissue surface proximate the cardiac opening. In another embodiment, the physician proximally withdraws the locator 628 by a fixed amount from the tissue surface of the cardiac opening to correctly position the balloon 700 within the cardiac opening.

The methods described above for positioning the balloon 700 within a cardiac opening apply equally to positioning the balloon 700 within a patent foramen ovale 44 or a left atrial appendage 80. Alternatively, other illustrative methods, specific to positioning a balloon 700 within a patent foramen ovale 44, are illustrated in FIGS. 33A-33E.

Figure 33A:
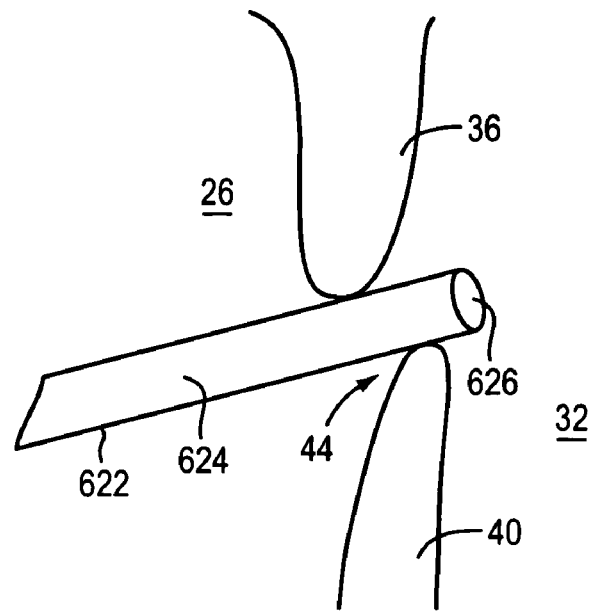
FIGS. 33A-33E illustrate the stages, according to another illustrative embodiment of the invention, for closing a patent foramen ovale in a patient.
Figure 33B:
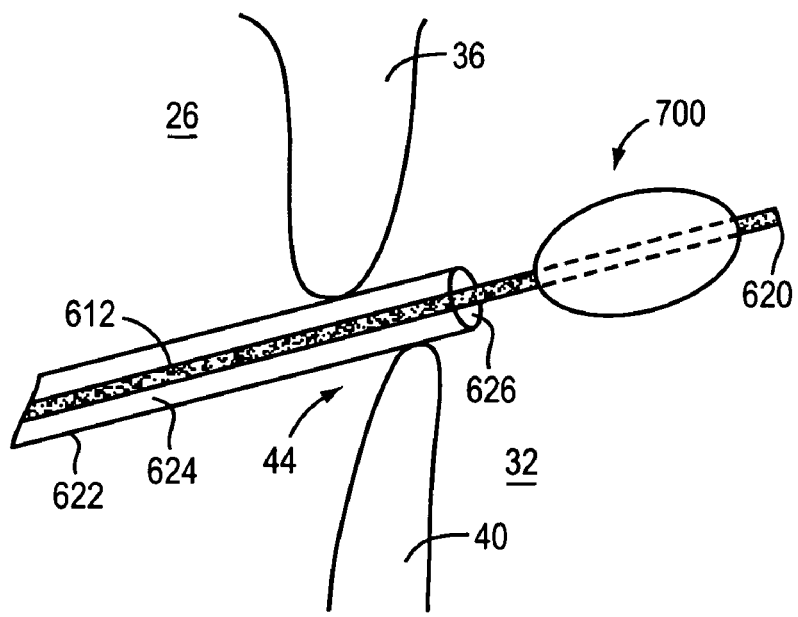

Referring first to FIG. 33A, in one embodiment, the physician advances the delivery catheter 622 into the patient's heart and through the patent foramen ovale 44, thereby positioning the distal end 626 of the delivery catheter 622 in the left atrium 32. The physician then advances the balloon 700 into and through the lumen 624 of the delivery catheter 622 until the balloon 700 and a distal portion of the balloon catheter 612 exit the distal end 626 of the delivery catheter 622 into the left atrium 32, as illustrated in FIG. 33B. After the balloon 700 exits the delivery catheter 622, the physician, in one embodiment, expands the distal locator 630, as illustrated in FIG. 33C.

Figure 33C:
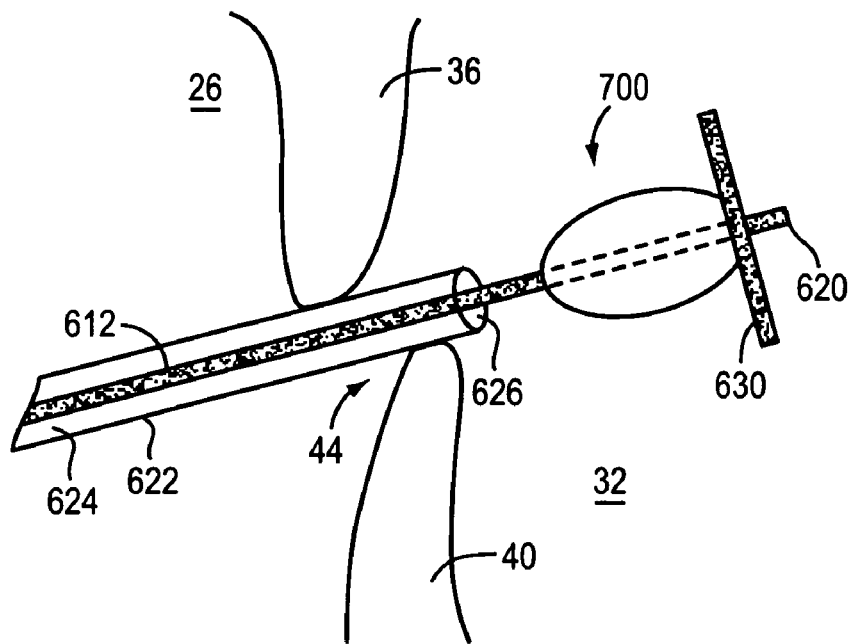

With the locator 630 expanded as illustrated in FIG. 33C, the physician withdraws the delivery catheter 622 and the balloon 700 proximally into the patent foramen ovale 44. The physician continues to withdraw the delivery catheter 622 and the balloon 700 into the patent foramen ovale 44 until the locator 630 abuts the distal walls of the septum secundum 36 and the septum primum 40, as illustrated in FIG. 33D.

Alternatively, in another embodiment, after the physician positions the distal end 626 of the delivery catheter 622 in the left atrium 32, as illustrated in FIG. 33A, rather than both deploying the balloon 700 and expanding the distal locator 630 in the left atrium 32, as illustrated in FIG. 33C, the physician only expands the locator 630 in the left atrium 32. The physician then positions the locator 630 to abut the distal walls of the septum secundum 36 and the septum primum 40. Once the locator 630 is positioned as such, the physician removes the delivery catheter 622 from about the balloon 700 to deploy the balloon 700 within the patent foramen ovale 44, as illustrated in FIG. 33D.

Figure 33D:
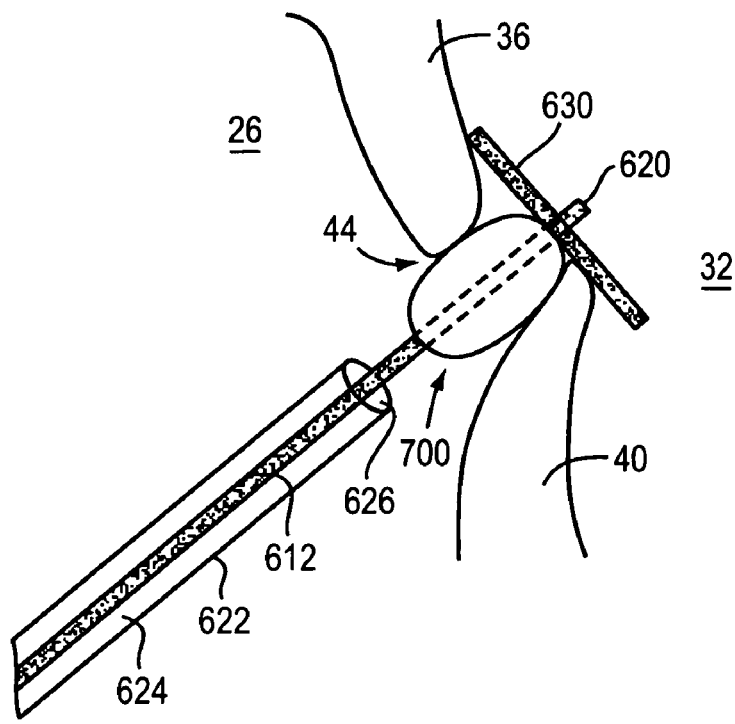
Figure 33E:
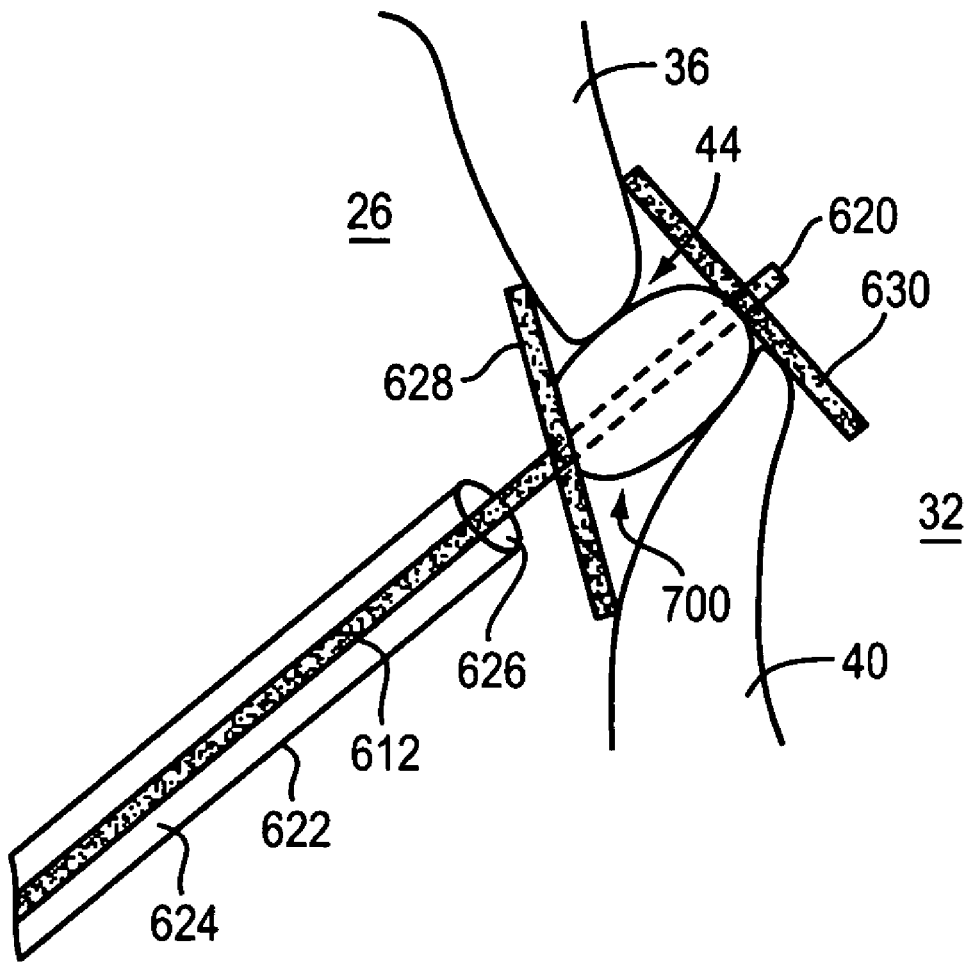

Optionally, when the balloon 700 is deployed within the patent foramen ovale 44 as illustrated in FIG. 33D, the physician then expands the proximal locator 628 in the right atrium 26, as illustrated in FIG. 33E. In one particular embodiment, the locators 628 and 630 are both balloons that are inflated in the right atrium 26 and the left atrium 32, respectively. Together, the locators 628 and 630 may be used to correctly locate and position the balloon 700 within the patent foramen ovale 44.

After the physician correctly positions the balloon 700 within the cardiac opening, as depicted in FIGS. 32D and 33E, the physician exposes the adhesive of the balloon 700 to the cardiac opening. As described above, the physician may accomplish this step in a variety of manners, depending on the type of balloon 700 that has been positioned within the cardiac opening.

In an exemplary embodiment, a deflated balloon 700$^f$ is positioned within the cardiac opening and, subsequent to placement within the cardiac opening, is inflated, as illustrated in FIG. 28. Where the balloon 700$^f$ includes the divider 1172 containing the primer 1184, the physician first applies the primer 1184 to the patient's tissue surface within the cardiac opening. In one embodiment, the physician does so by contacting the patient's tissues within the cardiac opening with the primer 1184 contained on the second surface 1180 of the divider 1172. The physician then removes the divider 1172 from about the balloon 700$^f$.

After applying the primer 1184 to the tissue surface of the cardiac opening and removing the divider 1172, the physician further inflates the balloon 700$^f$ to contact the tissue surface of the cardiac opening with the adhesive 1116A. Alternatively, where the balloon 700$^f$ does not include the divider 1172 and the primer 1184, the physician simply inflates the balloon 700$^f$ to contact the tissue surface of the cardiac opening with the adhesive 1116A immediately following the placement of the balloon 700$^f$ within the cardiac opening.

With the adhesive 1116A of the balloon 700$^f$ in contact with the patient's tissues in the cardiac opening, the physician activates the adhesive 1116A to cure the adhesive 1116A to the patient's tissues. In one embodiment, the physician illuminates the adhesive 1116A to activate the adhesive 1116A.

In various embodiments, once the adhesive is exposed to the tissue surface of the cardiac opening or the cardiac cul-de-sac, the physician allows the adhesive to cure and to thereby glue the balloon 700 to the tissue surface within the cardiac opening or the cardiac cul-de-sac. As such, the entire balloon 700 is coupled to the cardiac opening or the cardiac cul-de-sac to substantially occlude the cardiac opening or obliterate the cardiac cul-de-sac. Where, for example, the cardiac cul-de-sac is the left atrial appendage 80, the physician may couple the entire balloon 700 to the tissue surface of the left atrial appendage 80 to substantially obliterate the left atrial appendage 80. As another example, where the physician has positioned the balloon 700$^f$ within a patent foramen ovale 44 and activated the adhesive 1116A, the physician allows the adhesive 1116A to cure and to thereby couple the entire balloon 700$^f$ to the tissue surface of the patent foramen ovale 44. The physician may then separate and remove the balloon catheter 612 from the balloon 700$^f$ and deflate the balloon 700$^f$ to draw the septum secundum 36 and the septum primum 40 together. Once the balloon 700$^f$ is deflated, the adhesive 1116B, which is coated on the inner surface 1112 of the balloon 700$^f$, glues portions of the inner surface 1112 of the balloon 700$^f$ together.

Where the physician couples the entire balloon 700 to the cardiac opening, the physician may also couple the locators 628, 630 to the tissue surface of the patient proximate the cardiac opening. In one embodiment, for example, the physician uses the adhesive 632 to glue the locators 628, 630 to the tissue surface of the patient proximate the cardiac opening. The locators 628, 630 therefore also aid in closing the cardiac opening. Alternatively, one or both locators 628, 630 may be removed from the patient's body, even though the entire balloon 700 is coupled to the cardiac opening. For example, in one embodiment, the physician collapses the proximal locator 628 and removes it, along with the balloon catheter 612, from the patient's body. In another embodiment, the distal locator 630 is collapsed and proximally withdrawn, along with the balloon catheter 612, through the distal opening 635, through the lumen 631, and through the proximal opening 633 of the balloon 700 for removal from the patient's body.

In another embodiment, where the cardiac opening being closed is a patent foramen ovale 44, after the adhesive is exposed to the tissue surface of the patent foramen ovale 44 and is applied thereto, but before the adhesive has cured, the physician removes the balloon 700, the balloon catheter 612, and the one or more locators 628, 630 from the patent foramen ovale 44. In such a case, the natural pressure difference between the right atrium 26 and the left atrium 32 will eventually cause the septum secundum 36 to contact the septum primum 40. Because the septum secundum 36 and the septum primum 40 are coated with the adhesive, they will eventually bond together, thereby permanently closing the patent foramen ovale 44. Alternatively, in other embodiments, while removing the balloon 700 from the patent foramen ovale 44, the physician permanently glues one or both locators 628 and 630 to the tissue surface of the patient proximate the patent foramen ovale 44. The locators 628, 630 therefore also aid in closing the patent foramen ovale 44.

In yet another embodiment, the substance for stimulating tissue growth is combined with the adhesive of the balloon 700, or is used in place of the adhesive, and is delivered to, or impregnated within, the tissue surface of the patient's cardiac opening in a manner similar to that described above for the adhesives. In one embodiment, for example, the balloon 700 is used to deliver the growth substance to a patient's tissue surface located within a patent foramen ovale 44. The balloon 700 is then removed from the patent foramen ovale 44. The growth substance, having been applied to the septum secundum 36 and the septum primum 40, then stimulates tissue growth within the patent foramen ovale 44. The newly grown tissue leads to the closure of the patent foramen ovale 44.

Figure 34A:
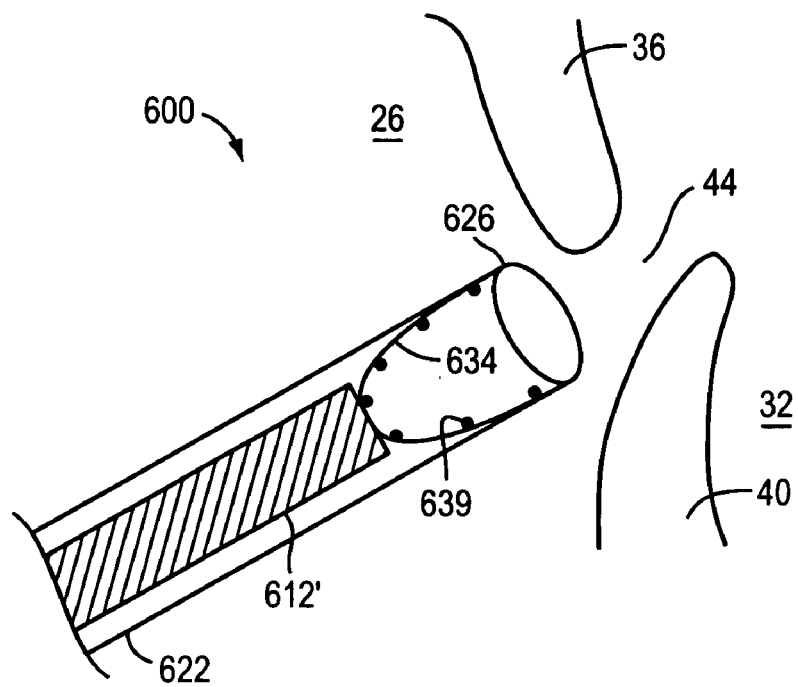
FIGS. 34A-34B illustrate the stages, according to another illustrative embodiment of the invention, for closing a patent foramen ovale in a patient.
Figure 34B:
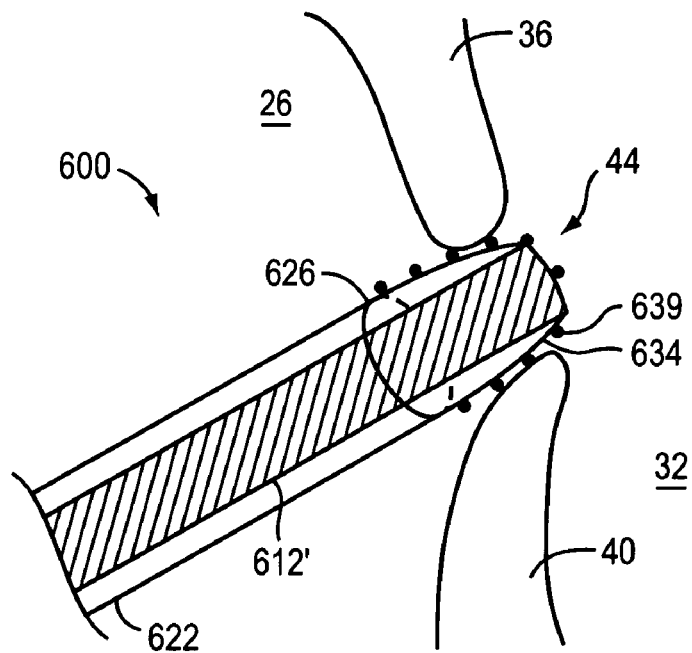

In yet another aspect, the invention provides methods for percutaneously closing a patent foramen ovale 44 using the exemplary closure system 600 depicted in FIGS. 30 and 31. In one embodiment, a physician advances the closure system 600 into the patient's heart with the sock catheter 612' retracted, as illustrated in FIG. 30. The physician then positions the distal end 626 of the delivery catheter 622 in the right atrium 26 proximate the patent foramen ovale 44, as illustrated, for example, in FIG. 34A. With the closure system 600 positioned as such, the sock catheter 612' is deployed to invert the lining 634 within the patent foramen ovale 44. Accordingly, as described above, the adhesive 639 and/or the substance for stimulating tissue growth is exposed to the patient's tissue surface located within the patent foramen ovale 44, as illustrated in FIG. 34B, and is applied thereto. The physician then retracts the sock catheter 612' to remove the lining 634 from the patent foramen ovale 44. Accordingly, as described above, the natural pressure difference between the right atrium 26 and the left atrium 32 causes the septum primum 36 and the septum secundum 30 to bond together, and/or natural tissue growth is stimulated within the patent foramen ovale 44, thereby leading to closure of the patent foramen ovale 44.

Variations, modifications, and other implementations of what is described herein will occur to those of ordinary skill in the art without departing from the spirit and the scope of the invention. The invention is not to be defined only by the preceding illustrative description.

What is claimed is:

1. A method for closing a patent foramen ovale in a patient, comprising:
    inserting a system for closing the patent foramen ovale into a heart of the patient via a percutaneous, transluminal procedure, the system comprising:
        a first catheter comprising a proximal end, a distal end, and a lumen extending from the proximal end to the distal end;
        a second catheter comprising a distal end, wherein the second catheter is movable between a retracted state where the distal end of the second catheter is enclosed within the lumen of the first catheter, and a deployed state where the distal end of the second catheter is extended beyond the distal end of the first catheter;
        a lining coupled to the distal end of the first catheter and the distal end of the second catheter, wherein the lining is positioned within the lumen of the first catheter when the second catheter is in the retracted state, and wherein the lining is inverted and is positioned outside the lumen of the first catheter when the second catheter is in the deployed state; and
        an adhesive material releasably sealed within the lining;
    positioning the system with the distal end of the first catheter proximate the right atrial side opening of the patent foramen ovale with the second catheter in the retracted state;
    inverting the lining into the patent foramen, by deploying the second catheter, thereby extending the distal end of the second catheter beyond the distal end of the first catheter;
    applying the adhesive to tissues of the patient in the patent foramen ovale by contacting the tissues with the inverted liner, wherein deploying the second catheter causes the adhesive to be released from the lining and exposed to the tissues of the patient;
    retracting the lining from the patent foramen ovale; and
    withdrawing the system from the patient.

2. The method of claim 1, wherein the lining comprises a plurality of holes or cavities comprising the adhesive.

3. The method of claim 1, wherein the lining further comprises a surface coating of adhesive.

4. The method of claim 1, wherein the lining is a balloon.

5. The method of claim 1, wherein the adhesive comprises a plurality of particles disposed within the adhesive that expand upon contact with blood or water.

6. The method of claim 5, wherein the particles are selected from the group consisting of gelatin particles, biological particles, bioresorbable particles, and foam particles.

7. The method of claim 1, wherein the adhesive is selected from the group of adhesives consisting of cyanoacrylates, fibrin based adhesives, albumin gluteraldehyde adhesives, and light activated adhesives.

8. The method of claim 1, wherein the adhesive comprises a substance for stimulating tissue growth.

9. The method of claim 8, wherein the substance for stimulating tissue growth is selected from the group consisting of growth factors, pharmacological agents for stimulating tissue growth, irritants for encouraging an inflammatory response, cells, and genes.

* * * * *